US008067531B2

(12) United States Patent  
Zhabilov

(10) Patent No.: US 8,067,531 B2
(45) Date of Patent: Nov. 29, 2011

(54) INACTIVATED PEPSIN FRAGMENTS FOR MODULATING IMMUNE SYSTEM ACTIVITY AGAINST HUMAN MALIGNANT TUMOR CELLS

(75) Inventor: Harry H. Zhabilov, San Marino, CA (US)

(73) Assignee: The Zhabilov Trust, San Marino, CA (US)

( * ) Notice: Subject to any disclaimer, the term of this patent is extended or adjusted under 35 U.S.C. 154(b) by 0 days.

(21) Appl. No.: 12/315,441

(22) Filed: Dec. 2, 2008

(65) Prior Publication Data

US 2010/0143291 A1 Jun. 10, 2010

Related U.S. Application Data

(63) Continuation-in-part of application No. 11/177,427, filed on Jul. 11, 2005, now Pat. No. 7,479,538.

(60) Provisional application No. 60/626,882, filed on Nov. 12, 2004, provisional application No. 60/635,938, filed on Dec. 15, 2004.

(51) Int. Cl.
C07K 5/00 (2006.01)
(52) U.S. Cl. ...................................... 530/300; 424/93.1
(58) Field of Classification Search ........................ None
See application file for complete search history.

(56) References Cited

U.S. PATENT DOCUMENTS

| 4,534,966 | A | 8/1985 | Ohnishi et al. |
| 5,002,766 | A | 3/1991 | Ransberger et al. |
| 5,436,143 | A | 7/1995 | Hyman |
| 5,872,210 | A | 2/1999 | Medabalimi |
| 6,165,794 | A | 12/2000 | Craik et al. |
| 6,461,615 | B1 | 10/2002 | Srivastava |
| 6,534,310 | B1 | 3/2003 | Craik et al. |
| 6,719,974 | B1 | 4/2004 | Rothman et al. |
| 6,979,566 | B2 | 12/2005 | Friedman et al. |
| 2002/0192797 | A1 | 12/2002 | Dash et al. |
| 2004/0005557 | A1 | 1/2004 | Padigaru et al. |
| 2004/0038330 | A1 | 2/2004 | Nagaoka |

FOREIGN PATENT DOCUMENTS

| AU | 678202 B | 12/1995 |
| WO | WO/2007/041285 | 12/2007 |

OTHER PUBLICATIONS

Rebecca L. O'Brien et al., "Heat Shock Protein Hsp60-reactive cells: A Large, Diversified T-lymphocyte Subset with Highly Focused Specificity" 5 pgs, Jan. 2, 1992.
Srivastava, P. (2002). Interactions of heat shock proteins with peptides and antigen presenting cells Annu. Rev. immunol. 20: 395-425.
Suzue K. and Young RA. Heat shock proteins as immunological carriers and vaccines. PubMed PMID 8856990. In: Stress-inducible Cellular Response, ed. U. Fiege, Birkhauser (1996) 77: 451-465.
Murray P. and Young RA. Stress and Immunological recognition in host-pathogen interaction. ,J Bacteriol (1992) vol. 174, No. 13, p. 4193-4196.
Suto, R. and Srivastava, P.K 1995. A mechanism for the specific immunogenicity of heat shock protein-chaperoned peptides. Science Sep. 15, 1995; 269; 1585-8.
Vabulas, R. M., Wagner, H. and Schild, H. (2002). Heat shock proteins as ligands of toll-like receptors. Curr. Topics Microbiol.lmmunol. 270; 169.
Sigal LJ., Crotty S., Andino R. and Rock KL. Cytotoxic T-cell immunity to virus-infected non-haematopoietic cell requires presentation of exogenous antigen. Nature (1999) 398:77 80.
Derky CS. Task force on recurrent respiratory papillomatosis. Arch Otolaryngol Head Neck Surg (1995) 121: 1386-1391.
Panjwani, N. N., Popova, L, Febbraio, M and Srivastava, P. K. (2001) CD91 is common receptor for heat shock proteins gp96, HSP 90, HSP70 and calreticulin. Immunity 14:303.
Srivastava, P. K., Deleo, A. B. and Old, L. J. Tumor rejection antigens of chemically induced sarcomas of inbred mice. Proc. Nat. Acad. Sci. USA. vol. 83:3407-11 May 1986.
Pockley, G. A. Heat Shock proteins in health and disease: therapeutic targets or therapeutic agents? Exp. Rev. Mol. Med. Sep. 21, 2001 http://www.ermm.cbcu.cam.ac.uk/01003556h.htm.
Parmiani, G. et al., Heat Shock Proteins and Their Use as Anticancer Vaccines. Clinical Cancer Research. vol. 10, 8142-8146. Dec. 15, 2004.
Gritti, I., Banfi, G., and Roi, G.S., Pepsinogens: Physiology, Pharmacology Pathophysiology and Exercise. Pharmacological Research. vol. 41. Nov. 3, 2000.
U.S. Appl. No. 10/336,512, filed Jan. 29, 2004, Zhabilov.
Lin, X-L. et al. Synthesis, Purification and Active Site Mutagenesis of Recombinant Porcine Pepsinogen, J. Biolog. Chem. Mar. 15, 1989, pp. 4482-4489, vol. 264, No. 8.
Filippova, I. et al. Fluorogenic Peptide Substrates for Assay of Asparty Proteinases, Analytical Biochemistry, Mar. 1996, pp. 113-118, vol. 234, see entire document.
Pockley, A. Heat Shock Proteins in Health and Disease: Theraputic Targets or Theraputic Agents?. Expert Reviews in Molucular Medicine. Sep. 21, 2001.
Sreedhar, A. et al. Heat Shock Proteins in the Regulation of Apoptosis: New Strategies in Tumor . . . Pharmacology & Therapeutics. Mar. 2004, pp. 227-257, vol. 101, No. 3.
Kamatari et al. Structural Dissection of Alkaline-denatured Pepsin. Science. 2003, pp. 717-724, vol. 12. Campos et al. The Active Site of Pepsin is Formed in the Intermediate Conformation Dominant at Mildly Acidic pH. FEBS Letters. 2003, pp. 89-95, vol. 538.
Harlow, E. et al. Antibodies: A Labratory Manuel, 1988, pp. 626-628, Cold Springs Harbor, NY.
Boyd, M.R. AIDS Etiology: Diagnosis, Treatment, and Prevention. Lippincott. 1988, pp. 305-319.

(Continued)

*Primary Examiner* — Bao Li
(74) *Attorney, Agent, or Firm* — Cislo & Thomas, LLP

(57) ABSTRACT

Isolated anti-cancer peptides are disclosed which are characterized by the amino acid sequences TLTSGGGAIALPPS-MAAPPLGPVAPLTGAIHAPTXG; TLSTATGGAIP-PVAAMPPGLVAPTHGPAIHP; CCATSGPCGAVMILTPHLTA; MTLTTGSGAIAPAMP-PGLPPHTGAIHAPM; and NXVPVSVEGYXQITLDSITX and a significant in vitro binding affinity for gp96. The peptides exhibit anti-tumor, anti-cancer activity in vivo. Also disclosed is an isolated antiviral peptide is characterized by the amino acid sequence GDEPLENYLDTEYF and a significant in vitro binding affinity for HIV-1 gp 120 and gp 41, and human CD4 cells. The peptide exhibits anti-retroviral activity in vivo, particularly anti-HIV-1 activity.

8 Claims, 10 Drawing Sheets

OTHER PUBLICATIONS

Sigal, L. et al. Cytotoxic T-cell Immunity to Virus-Infected Non-haematic Cells . . . , Nature, 1999, pp. 77-80, Issue 398.

Gulakowski, R., Laboratory of Drug Discovery Research and Development, Journal of Virological Methods, Jun. 1991, pp. 87-100, vol. 33, No. 1-2.

Tang, J. et al., Amino-Acid Sequence of Porcine Pepsin, Proceedings of the National Academy of Sciences, Dec. 1973, pp. 3437-3439, vol. 70, No. 12.

Weissenhorn, W. et al., Atomic Structure of the Ectodomain from HIV-1 gp41, Nature, May 22, 1997, pp. 426-430, No. 387.

Kirk, R., et al., A Nonpromoting Phorbol from Samoan Medicinal Plant *Homalanthus Nutans* . . . , Journal of Medicinal Chemistry, 1992, pp. 1978-1986, vol. 35, No. 11.

Moore, J. et al., HIV Envelope's Letters Boxed into Shape, Nature, Jun. 18, 1998, pp. 630-631, No. 393.

Weislow, O. et al., New Soluable-formazan Assay for HIV-1 Cytopathic Effects . . . , Journal of the National Cancer Institute, Jun. 21, 1989, p. 963, vol. 81, No. 12.

Laemmli, U., Cleavage of Structural Proteins During the Assembly of the Head Bacteriophage T4, Nature, Aug. 15, 1970, pp. 680-685.

Pockley, A., Heat Shock Proteins in Health and Disease . . . (Figure 4), Expert Reviews in Molecular Medicine, Sep. 21, 2001.

Radsak, M., The Heat Shock Protein Gp96 Binds to Human Neutrophils and Monocytes and Stimmulates Effector Functions, Blood, Apr. 1, 2003, pp. 2810-2815, vol. 101, No. 7.

Weissenhorn, W., Structural Basis for Membrane Fusion by Envelope Viruses, Molecular Membrane Biology, Jan. 1, 1999, pp. 3-9, vol. 1, No. 1.

Supplementary European Search Report, EP 05 85 0002, Oct. 1, 2010.

Sogawa K et al: "Molecular Cloning of Complementary DNA to Swine Pesinogen Messenger RNA", Journal of Biological Chemistry, vol. 256, No. 23, 1981, pp. 12561-12565.

Tanaka T et al: "N-terminal portion acts as an initiator of the inactivation of pepsin at neutral pH." Protein Engineering Sep. 2001, vol. 14, No. 9, pp. 669-674.

Jiang S et al: "Peptide and Non-Peptide HIV Fusion Inhibitors," Current Pharamecutical Design, Bentham Science Publishers, vol. 8, No. 8, Jan. 2002, pp. 563-580.

Yu F.I. et al: "Fluorogenic Peptide Substrates for Assay for Aspartyl Proteinases," Analytical Biochemistry. vol. 234, Mar. 1996, pp. 113-188.

Porcine pepsinogen sequence:

| | | |
|---|---|---|
| SEQ ID: NO. 11 | MKWLLLLSLV VLSECLVKVP LVRKKSLRQN LIKNGKLKDF LKTHKHNPAS KYFPEAAALI GDEPLENYLD | Pig |
| SEQ ID: NO. 12 | IGDEPLENYLD | |
| SEQ ID: NO. 13 | IEYFGTIGIG TPAQDFTVIF DTGSSNLWVP SVYCSSLACS DHNQFNPDDS STFEATSQEL SITYGTGSMT | Pig |
| SEQ ID: NO. 14 | TEYF--45K IPF-P1 | |
| SEQ ID: NO. 15 | GILGYDTVQV GGISDTNQIF GLSETEPGSF LYYAPFDGIL GLAYPSISAS GATPVFDNLW DQGLVSQDLF | Pig |
| SEQ ID: NO. 16 | S GATPZIE -30K CP | |
| SEQ ID: NO. 17 | SYMLSSNDDS GSWLLGGID SSYTGSLNW VPVSVEGYWQ ITLDSITMDC ETIACSGGCQ AIVDTGTSLL | Pig |
| SEQ ID: NO. 18 | NX VPVSVEGYXQ ITLDSITX-15K IPF-P1 | |
| SEQ ID: NO. 19 | LGGID SSYTGSLNW VPVSVEGYWQ IT-20K CP | |
| SEQ ID: NO. 20 | SYYTGSLNIR VPVSVEGYWQ ITLDSITM-20K CP | |
| SEQ ID: NO. 21 | SYYTGSLNW VPVSVEGYWQ ITLDSI-15K CP | |
| SEQ ID: NO. 22 | NW VPVSVEGYWQ ITLDSIIMDG RTI-15K CPL | |
| SEQ ID: NO. 23 | IGPTSAIAIN IQSDIGASEN SDGEMVISCS SIDSLPDIVF TINGVQYPLS PSAYILQDDD SCTSGFEGNm | Pig |
| SEQ ID: NO. 24 | VPTSSGELWI LGDVFIRQYY IVFDRANNKV GLAPVA | Pig |
| SEQ ID: NO. 25 | GDEPLENYLDTEW--from 45 kDa band of IPF-P i prep | |
| SEQ ID: NO. 26 | NWPVSVEGYXQITLDSITX--from 15 kDa band of IPF-P1 prep | |
| SEQ ID: NO. 27 | SGATPVF-30K CP [CLP] | |
| SEQ ID: NO. 28 | LGGIT7SSYTGSLNWPVSVEGYWQIT--20K CP (primary sequence) | |
| SEQ ID: NO. 29 | SYYTGSLNWPVSVEGYWQITLSDITM--20K CP (minor sequence) | |
| SEQ ID: NO. 30 | SAYTGSLNWPVSVEGYWQITLDSI--15K CP (primary sequence) | |
| SEQ ID: NO. 31 | NWPVSVEGYWQITLDSIIMDGRTI--15K CP (minor sequence) | |

FIG. 1

Amino Acid Normalization

| Amino Acid | aaa350 | nmoles aa | μgrams | mole percent | # residues |
|---|---|---|---|---|---|
| cysac | | | | | |
| cmcys | | | | | |
| asx | 22.8877 | 22.888 | 2.634 | 12.0% | 52.4 |
| thr | 12.4691 | 12.469 | 1.261 | 6.5% | 28.6 |
| ser | 18.8294 | 18.829 | 1.640 | 9.8% | 43.1 |
| glx | 17.3625 | 17.363 | 2.224 | 9.1% | 39.8 |
| pro+cys | 14.1223 | 14.122 | 1.372 | 7.4% | 32.3 |
| gly | 30.3407 | 30.341 | 1.731 | 15.9% | 69.5 |
| ala | 11.6156 | 11.616 | 0.826 | 6.1% | 26.6 |
| val | 11.7925 | 11.793 | 1.169 | 6.2% | 27.0 |
| met | 2.0077 | 2.008 | 0.263 | 1.1% | 4.6 |
| ileu | 12.4881 | 12.488 | 1.413 | 6.5% | 28.6 |
| leu | 13.8494 | 13.849 | 1.567 | 7.2% | 31.7 |
| tyr | 8.7045 | 8.705 | 1.420 | 4.6% | 19.9 |
| phe | 7.6939 | 7.694 | 1.132 | 4.0% | 17.6 |
| his | 1.5271 | 1.527 | 0.209 | 0.8% | 3.5 |
| lys | 2.6238 | 2.624 | 0.336 | 1.4% | 6.0 |
| trp | | | | | |
| arg | 2.8688 | 2.869 | 0.448 | 1.5% | 6.6 |
| % injected | 100% | | | total residues: | 438 |

Sample: IPF
% loaded: 25%
MW: 45,000

| | μg |
|---|---|
| Analyzed | 19.647 |
| Sample total | 78.586 |

| nmol protein |
|---|
| 0.4366 |
| 1.7464 |

(w/o Cys, Trp)

SAMPLE NAME: I

SEQ ID NO. 8
THR
LEU
TYR
SER
GLY
GLU
GLN
ASP

SEQ ID NO. 9
ARG
LYS
PHE

SEQ ID NO. 10
SER
MET
ASN
ASP

| SEQUENCE: | ILE | — | PRO | — | PHE | PRO | PHE | — | ASN | HIS |
| --- | --- | --- | --- | --- | --- | --- | --- | --- | --- | --- |
| | | | | | LEU | VAL | LEU | | ILE | ALA |
| | | | | | GLU | ASP | TYR | — | GLY | — |
| CYCLE #: | 1 | | 2 | | 3 | 4 | 5 | 6 | 7 | 8 | 9 |

MET

| SEQUENCE: | PHE | — | THR | — | X | GLY |
| --- | --- | --- | --- | --- | --- | --- |
| CYCLE #: | 10 | | 11 | | 12 | 13 |

YIELD (pmol): GLU (4) 342.49%   YIELD (pmol): ASP (5) 257.55
CARRYOVER: GLU (4) 10.1%   PERCENT LOADED: 1UL
SEQSTD YIELD: NL (6) 3.10   SEQSTD CARRYOVER: NL (6) 14.2%
SEQSTD REP YIELD: NL(6,11) 81.4%

COMMENTS: COMPLEX MIXTURE. AMINO ACIDS INTERCHANGEABLE AT MOST CYCLES. LEVEL OF SEQUENCING
DROPPED OFF AFTER CYCLE 5. VARIOUS COMBINATIONS OF AMINO ACIDS HAVE SIMILARITY
WITH PORCINE PEPSIN.

PINK HIGHLIGHTED AMINO ACIDS:    RESIDUES 20-22
ORANGE HIGHLIGHTED AMINO ACIDS:  RESIDUES 63-75
BLUE HIGHLIGHTED AMINO ACIDS:    RESIDUES 32-37
GREEN HIGHLIGHTED AMINO ACIDS:   RESIDUES 60-67
PURPLE HIGHLIGHTED AMINO ACIDS:  RESIDUES 100-103
YELLOW HIGHLIGHTED AMINO ACIDS:  RESIDUES 222-229

FIG. 11

INACTIVATED PEPSIN FRAGMENTS FOR MODULATING IMMUNE SYSTEM ACTIVITY AGAINST HUMAN MALIGNANT TUMOR CELLS

CROSS-REFERENCE TO RELATED APPLICATIONS

This utility patent application is a continuation-in-part application of, and claims priority from, pending U.S. Utility application Ser. No. 11/177,427 filed on Jul. 11, 2005 now U.S. Pat. No. 7,479,538 and entitled "Irreversibly-inactivated Pepsinogen Fragment and Pharmaceutical Compositions Comprising the Same for Detecting, Preventing, and Treating HIV", the disclosure of which is incorporated herein in its entirety by reference, which in turn claims priority from Provisional Application Nos. 60/626,882 and 60/635,938 filed on, respectively, Nov. 12, 2004 and Dec. 15, 2004.

FIELD OF THE INVENTION

The present invention relates to compositions and methods comprising an inactivated pepsin fragment ("IPF") for modulating immune system activity. More specifically, embodiments of the present invention are directed to compositions and methods to elicit specific immunity to recognize peptides associated with tumors and malignancies. The present invention also relates to compositions and methods comprising IPF for treating infections such as infection by the human immunodeficiency virus.

BACKGROUND OF THE INVENTION

Pepsin is a proteolytic enzyme produced in the mucosal lining of the stomach and acts to degrades protein, together with chymotrypsin and trypsin. During digestion, these enzymes, each of which is effective in severing links between particular types of amino acids (e.g. phenylalanine, tryptophan and tyrosine), collaborate to break down dietary proteins to their components, i.e., peptides and amino acids.

Current studies indicate that immune protection against cancer requires the generation of a potent cellular immune response against a unique tumor antigen expressed by a malignant cell. Thus, successful immune protection would first require identifying a unique antigen in the tumor cells (tumor specific antigen) and then inducing a potent T-cell response targeted to the tumor antigen. These tumor-associated antigens, however, would still be recognized by immune cells as 'self' molecules, and so no true activation of the immune system would occur. Thus, two obstacles in targeting these tumor-associated molecules as a vaccine include the unresponsiveness of the immune system to 'self' molecules, which restricts its ability to generate potent cellular immune responses, and preventing the generated immune response from being directed to normal cells that express the target antigen.

Proteins that show promise in overcoming these problems include heat shock proteins (HSPs). HSPs include a collection of ubiquitously expressed cytoprotective proteins, which are expressed by cells under conditions of cell stress, such as increased temperature, viral infection and oxidative stress. Certain HSPs have been shown to have immunomodulatory effects, such as the induction of cytokines and the promotion of cell activation and maturation (see, Pockley A G, Lancet 363 (9382) 469-476 (2003)).

For example, Zheng et al. (2001) report that cell surface targeting of HSP gp96 induces dendritic cell maturation and antitumor immunity as demonstrated by the expression of immune factors such as interleukins and certain cell surface antigens (e.g., CD40, CD80 and MHC class II antigens). It has been known for some time that heat shock proteins bind peptide and that heat shock proteins purified from cells chaperone a large number of peptides derived from the cells from which they are isolated. This is the so-called 'antigenic repertoire' of that cell. Studies have demonstrated that immunizing mice with HSP70, HSP90 and gp96 isolated from murine tumor cells induces anti-tumor immunity and tumor-specific cytolytic T-cells. These studies also show that the immunity results from tumor-derived peptides associated with the heat shock protein rather than from the heat shock proteins themselves. More recently, studies reported the use of calreticulin, HSP110 and grp170 in heat shock protein-based cancer immunotherapy. Specific immunogenicity of tumor-derived heat shock protein preparations have been studied in relation to fibro sarcomas, lung carcinoma, prostate cancer, spinal cell carcinoma and melanomas in mice and rats of different haplotypes. These studies included chemically-induced tumors, UV-induced tumors, and spontaneous tumors. Heat shock proteins show promise in that preparations isolated from a given cell may be associated with a range of peptides, including self and antigenic peptides and in that HSP-peptide complexes are highly immunogenic.

Certain heat shock proteins demonstrate "superantigen" activity. They are capable of activating large numbers of T-lymphocytes in a major histocompatibility complex-restricted manner. This polyclonal activation of certain T-cell subsets may be responsible for some of the immunomodulatory effects. These components have been reported to stimulate immune responses to certain neoplasms and may be involved in the pathogenesis of certain autoimmune diseases.

Gp96 is a HSP of particular interest. Gp96 is a 96 kDa glycoprotein localized to the endoplasmic reticulum, which can also be found at the cell surface. Gp96 is released into the extra cellular space during necrotic cell death and activates dendritic cells and macrophages by realizing inflammatory cytokines and inducing dendrites cells to mature. Gp96 has the ability to transfer antigenic peptides for their MHC-class I-restricted presentation and allows gp96 to function as an efficient messaging system alerting the immune system of an infection. This includes the receptor-mediated uptake of gp96 by dendrite cells. The receptor is CD91, which is known as the α2 macroglobulin (α2M) receptor expressed on phagocytes. The presentation of gp96-associated peptide by antigen-presenting cells ("APC's") is induced by α2 macroglobulin. Gp96 is bound by CD91 on dendrite cells and internalized. Gp96 induces the expression of co-stimulatory molecules and the release of interleukin 12 (IL-12) and tumor necrotic factor α ("TNFα") by the APC.

Certain infections, such as by the human immunodeficiency virus, have also presented challenges in targeting the disease-causing organism and neutralizing it. Typically, infection with the human immunodeficiency virus, HIV-1, eventually causes acquired immunodeficiency syndrome (AIDS) and an associated syndrome, AIDS-related complex (ARC). Neutralizing this virus has proved difficult, largely because its structure obstructs immune system access to viral epitopes and its genetic material is highly variable. Accordingly, researchers have been seeking prophylactic and therapeutic methods for preventing or controlling HIV which are not dependent upon antibody-mediated immunity.

The HIV retrovirus replicates in certain immune system cells, specifically the CD4+ subset of T-lymphocytes (pre-Th cells arising in the thymus). In the usual course of a cell-mediated immune response to an intracellular pathogen such as a virus, dendritic cells (antigen-presenting cells) carrying antigen fragments and secreted cytokines activate these CD4+ T-cells. Activated cells, called T-helper or Th cells, in turn secrete their own cytokines and stimulate macrophages. CD4+Th cells also propagate cellular immune response by binding chemotactic cytokines (chemokines, CCs) to their CC surface receptors. It is by this route that HIV-1 infection of these cells is enabled because, in addition to binding chemokines, these CC receptors act together with the CD4+ surface glycoprotein as co-receptors for HIV-1 and mediate entry of the virus into the CD4+Th cell. There, the virus usurps the native genetic material for viral replication while destroying cell functions essential for building immunity; the increasing destruction of these cells appears to be responsible for the eventual collapse of the cell-mediated immune system often seen in terminal AIDS patients.

It has been recognized that denying entry into CD4+ cells to the HIV-1 virus could at least slow the progress of the infection and alleviate, if not cure, the disease and/or its symptoms. The complex mechanism by which the virus crosses the cell membrane has been widely investigated. Broadly, the entry of human immunodeficiency virus into, for example, CD4+ Th1 cells (T-helper type 1 cells), is dependent upon a sequential interaction of the gp120/gp41 subunits of the viral envelope glycoprotein gp160 with the CD4+Th1 cell surface glycoprotein and the cell surface receptor CCR5. On binding of gp120 with its cell surface binding sites, a conformational change in the latent gp41 subunit through an intermediate state to an active state is initiated, inducing fusion of the viral and cellular membranes and transport of the virus into the cell (Weissenhom et al., *Nature*, 387:426-30 (1997)).

Accordingly, numerous binding experiments have been conducted in an effort to find antiviral ligands that will effectively compete with the HIV-1 for CD4+ gp and/or CCR5 binding sites, or that will preferentially block gp120 and/or gp41 binding domains. In one example, a reported structure (X-ray crystallography) comprising an HIV-1 gp120 core complexed with a two-domain fragment of human CD4 and an antigen-binding fragment of a neutralizing antibody that blocks chemokine-receptor binding, is said to reveal a CD4-gp120 interface, a conserved binding site for the chemokine receptor, evidence for a conformational change on CD4 binding, the nature of a CD4-induced antibody epitope, and specific mechanisms for viral immune evasion, "which should guide efforts to intervene" (*Nature* 393 (6686):632-1, 1998). Also, it has been shown that inhibition of the change in structure of gp41 from its intermediate to active state with peptides used as competitors for critical cell receptors may reduce viral load, and that while gp120 masks epitopes on the gp41 subunit in its latent state, gp41 may be vulnerable to neutralizing antibodies in its transient or intermediate state (*Molecular Membrane Biology* 16:3-9, 1999).

BRIEF DESCRIPTION OF THE DRAWINGS

Some aspects of the present invention are generally shown by way of reference to the accompanying drawings in which:

FIG. 1 illustrates the porcine pepsinogen sequence, and major and minor sequences of this pepsinogen.

FIG. 10 shows amino acid normalization for the 45 kDa IPF fragment according to one embodiment of the invention.

FIG. 11 shows sequencing results and yields for pepsin fragments relating to SEQ ID: NO. 1 according to one embodiment of the invention.

SUMMARY OF THE DISCLOSURE

Figure 2:
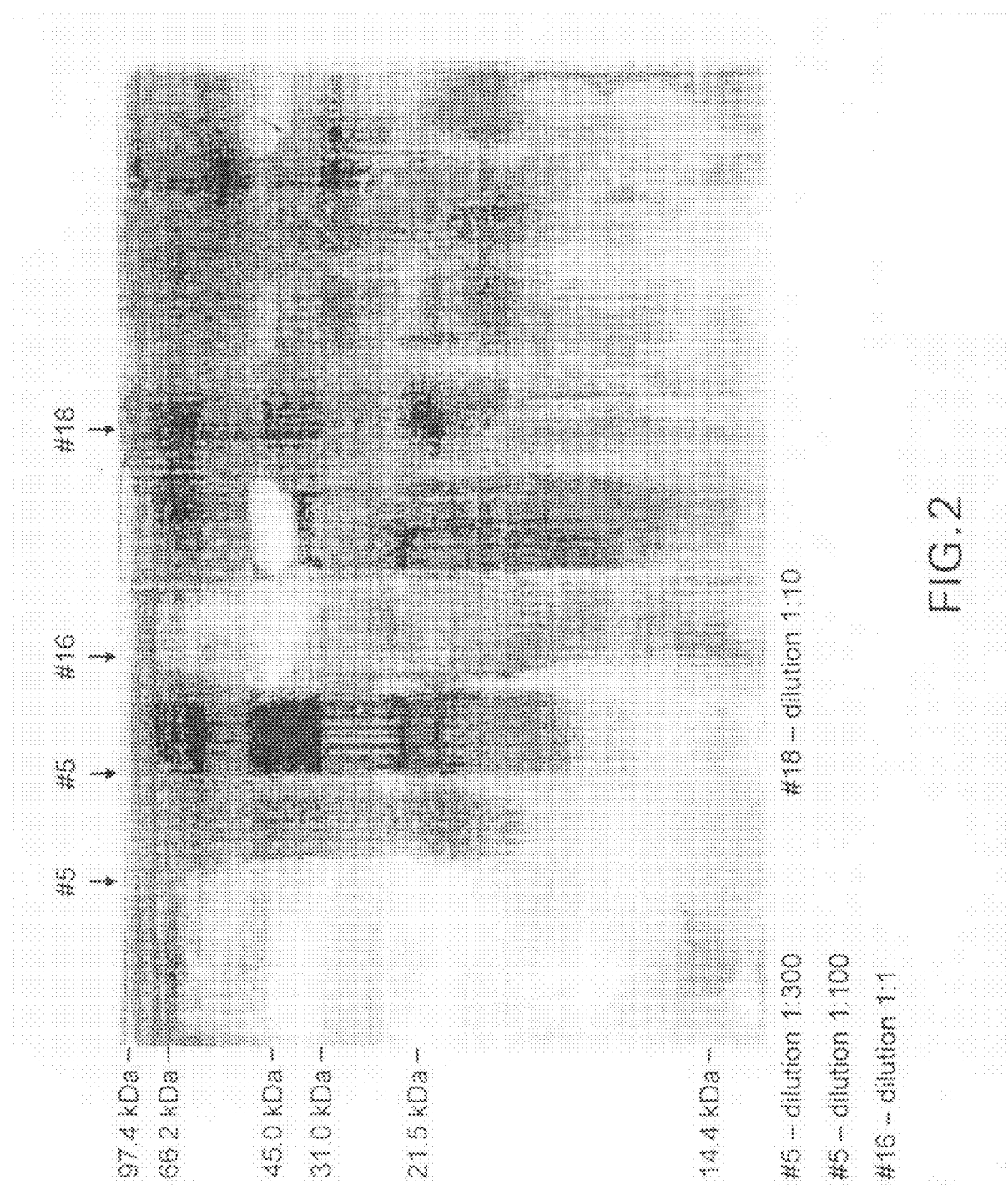
FIG. 2 is a photograph of an electrophoresis gel showing an inactivated pepsinogen fragment ("IPF") in the 45.0 kDa band. SDS-PAGE was used for determination of molecular weight of the components of IPF. Column 1 included weight standards shown in the box to the left. The next two columns show #5, bovine albumin, at 1:300 dilution and 1:500 dilution. The remaining columns show samples 16-21 at various concentrations. Sample 16 was obtained from porcine pepsin Sigma p7000 1:10000 purified and methylated. Samples 17 and 21 were prepared as with Sample 16. Sample 18 was porcine pepsin Sigma p7000 1:10000, diluted in buffer at pH 3.2, so that pepsin is an active protease. Sample 19 was obtained from porcine pepsin Sigma p7000 1:10000 and purified, but unmethylated. Sample 20 was prepared as with Sample 19. The next columns, in order, show methylated IPF sample #16 at a 1:1 dilution, methylated IPF sample #17 at a 1:1 dilution, untreated pure (active) pepsin sample #18 at a 1:10 dilution, unmethylated IPF sample #19 at a 1:10 dilution, unmethylated IPF sample #20 at a 1:10 dilution, and methylated IPF sample #21 at a 1:10 dilution. IPF samples #16, 17, and 21 include as a major component a protein/peptide migrating with an apparent molecular weight of 45 kD. These samples show highly specific binding between IPF and gp41, gp120, and CD4 at different concentrations.

The present invention includes methods and compositions comprising modified cellular shock protein gp96 which preferably includes an irreversible pepsin fraction IPF and more preferably includes an IPFgp96 complex. In another preferred embodiment, a complex of IPFgp96 may be combined with at least one other polynucleotide like a molecular adjuvant, such as IL-2, to increase cellular immune response.

Preliminary clinical trials have demonstrated the induction of cancer specific CD8+ T-cells responses in 6/12 patients immunized with gp96-peptide prepared from their own tumor. The capacity of tumor-derived heat shock proteins to induce specific and protective immunity might have profound effects on the treatment and management of patients with malignant disease. For example, studies have shown that induction of immunity to methylcholanthrane-induced fibro sarcoma by the administration of gp96 isolated from the tumor displays consistent dose restriction: two intradermal administrations of <1 μg gp96 was found to be ineffective; two doses of 1 μg was found to induce immunity and provide optimal protection against tumor growth; and two doses of 10 μg was found not to protect.

The lack of protection at high doses of tumor-derived gp96 is an active, antigen specific down-regulation of tumor-specific immunity that can be adoptively transferred by CD4 T-cells purified from animal treated with high doses of tumor derived gp96. These findings are exciting as they suggest that immunization with heat shock proteins that are chaperoning clinically relevant peptides might be an effective strategy for down regulating several diseases including autoimmunity.

The addition of IL-2 to activate normal human lymphocytes directly promotes several other cellular functions as well as proliferation. IL-2 stimulated T-cells exhibit enhanced cytotoxicity and produce lymphokins such as INF-γ TNF-β and TGF-β; B-cells growth factors such as IL-4 and IL-6 and GM-CSF. IL-2 also induces lymphokine-activated killer (LAK) activity, which is predominantly due to NK cells.

The present invention also encompasses a cancer preventive or therapeutic vaccine comprising a IPFgp96 complex, and more specifically complexes of IPF-1gp96; IPF-2gp96; IPF-3gp96, IPF-4gp96, IPF-5gp96, singly or in combinations thereof, which may be mixed with one or more polynucleotides encoding a molecular adjuvant. Any molecular adjuvant that increases cellular immune response may be used like cytokine IL-2. In the preferred embodiments, the compositions and methods of the present invention comprise binding between IPF fragments and receptors of gp96, such as for example, CD91, in vivo. Administration may be via an intramuscular injection. The cancer to be treated may be primary or metastatic and the patients to be treated may have multiple different types of cancer.

IPF has been shown to have an ability to modulate Th1 immunity, cytokine secretion and γIFN. Placebo and controlled double blind assay using two groups of rats show immunological changes following active therapy, which were sustained over time. These changes include: 1) increase in the CD4+ CD45RO+ CD62 L population; 2) increase in the CD4+ CD45RA+ CD62 L population; 3) appearance of a second CD4+ population having lower CD4 intensity but no increase in SSC, implying a second CD4 cell population. Preliminary studies of this population in isolation reveals that these cells are not memory or naïve cells; 4) a parallel increase in absolute CD4 cell counts; 5) an increase in CD8+ CCR5+ population.

In addition, functional assays showed the following: 1) an increase in the IFN-[y] containing CD3+ CD4+ cells post stimulation in vitro; 2) a decrease in the IL-4 containing CD3+ CD4+ cells post-stimulation; 3) a significant increase in the IFN-γ containing CD3+ CD8+ cells over time.

Also, numerous binding experiments have been conducted in an effort to find antiviral ligands that will effectively compete with the HIV-1 for CD4+ gp and/or CCR5 binding sites, or that will preferentially block gp120 and/or gp41 binding domains. In one example, a reported structure (X-ray crystallography) comprising a HIV-1 gp120 core complexed with a two-domain fragment of human CD4 and an antigen-binding fragment of a neutralizing antibody that blocks chemokine-receptor binding, is said to reveal a CD4-gp120 interface, a conserved binding site for the chemokine receptor, evidence for a conformational change on CD4 binding, the nature of a CD4-induced antibody epitope, and specific mechanisms for viral immune evasion, "which should guide efforts to intervene" (*Nature* 393 (6686):632-1, 1998). Also, it has been shown that inhibition of the change in structure of gp41 from its intermediate to active state with peptides used as competitors for critical cell receptors may reduce viral load, and that while gp120 masks epitopes on the gp41 subunit in its latent state, gp41 may be vulnerable to neutralizing antibodies in its transient or intermediate state (Molecular Membrane Biology 16:3-9, 1999).

Other embodiments of the present invention are generally directed to providing pharmaceutical compositions comprising IPF (IPF-1, IPF-2, IPF-3, IPF-4, IPF-5 and/or IPF-6) and methods for preventing, treating, and diagnosing HIV-1 infections and HIV-1 related conditions such as AIDS (Acquired immune Deficiency Syndrome) and ARC (AIDS Related Complex) with these compositions.

In an exemplary embodiment the present invention relates to a method of modulating immune system activity comprising administering to a patient an effective amount of a composition containing inactivated pepsin fragment (IPF).

The isolation, purification and characterization and a variety of other uses, e.g., diagnosis and treatment of HIV infection and related diseases such as AIDS and ARC, of the inactivated pepsin fragment or fraction (IPF) as used herein is described in commonly owned U.S. Provisional Patent Application No. 60/644,054, filed Jan. 18, 2005, Zhabilov, the contents of which are incorporated herein by reference in their entirety.

At least 8 isozymes of pepsinogen have been identified in gastric epithelial cells, and these have been categorized into two immunologically-separable types (pepsins A and C). The mature, active enzymes are roughly 325 amino acids with a mass of approximately 35 kDa. Pepsins are synthesized as inactive pre-proenzymes, consisting of a signal peptide, activation peptide and active enzyme. The signal peptide is cleaved as the protein is inserted into endoplasmic reticulum and the resulting proenzyme—pepsinogen—is transported to the Golgi and condensed into secretory granules. Pepsinogens are secreted in a form such that the activation peptide assumes a compact structure that occludes the active site. On exposure to an acidic (pH <4) environment such as occurs in the lumen of the stomach, the activation peptide unfolds, allowing the active site to clip it off, yielding mature, catalytically active pepsin.

Structurally, the active site is located in a deep cleft within the molecule located between two homologous portions of the structure, the N-terminal lobe (residues 1-172) and the C-terminal lobe (residues 173-327). Optimal activity of pepsins is at pH of 1.8 to 3.5, depending on the isoform. They are reversibly inactivated at about pH 5 and irreversibly inactivated at about pH 6 to 7 or 7 to 8. See, Yuji O. Kamatari, Christopher M. Dobson, and Takashi Konno, "Structural dissection of alkaline-denatured pepsin," *Protein Science* (2003), 12:717-724.

According to Entrez Protein, accession number NP_999038, a sequence of swine porcine pepsinogen is SEQ ID NO:7:

```
000 mkwllllslv vlseclvkvp lvrkkslrqn likngklkdf lkthkhnpas kyfpeaaali
061 gdeplenyld teyfgtigig tpaqdftvif dtgssnlwvp svycsslacs dhnqfnpdds
121 stfeatsqel sitygtgsmt gilgydtvqv ggisdtnqif glsetepgsf lyyapfdgil
181 glaypsisas gatpvfdnlw dqglvsqdlf svylssndds gsvvllggid ssyytgslnw
241 vpvsvegywq itldsitmdg etiacsggcq aivdtgtsll tgptsaiain iqsdigasen
301 sdgemviscs sidslpdivf tingvqypls psayilqddd sctsgfegmd vptssgelwi
361 lgdvfirqyy tvfdrannkv glapva
```

According to Kamatari et al., after the N-terminal 60 bases of pepsinogen are cleaved off to produce pepsin, the N-terminal lobe of pepsin protein includes residues 1-172, and the C-terminal lobe includes the remaining residues 173-326. IPF-6 according to the invention differs from pepsin. It includes a major component having an apparent MW of 45 kD when subjected to SDS-PAGE as shown in FIG. 2. It is unclear whether the 45 kD IPF-6 peptide is actually larger than pepsin, e.g. due to dimerization or other bonding with itself or another peptide, or whether the 45 kD apparent molecular weight is an artifact due to chemical modification of the protein such as methylation. The term "45 kD IPF-6" is used here to refer to the IPF-6 molecule obtained and assayed as described here, whether its actual molecular weight is 45 kD or another figure.

Surprisingly, preparations isolated from pepsin provide highly sensitive, specific, and therapeutic biological preparations. The starting material may be pure, active porcine pepsin A. An exemplary starting material is Sigma porcine pepsin P 7000, which has a concentration of 1:10000. Other starting material preparations are acceptable and may be effective according to the invention, if treated and isolated according to the invention. For example, porcine pepsin with other concentrations may be used e.g. 1:60000. The starting material is preferably white to yellow, not brown, and may have a milk-like smell.

Other natural or recombinant sources of pepsin may be used, or other similar aspartic proteases, provided that the protease is inactive at alkaline, neutral, near-neutral, or mildly acidic pH, has a pI in those ranges, and has a sequence with substantial homology to the IPF 45 kD fragment reported here. Substantial homology means at least about 50, 60, 70, 80, 90, or 95% identity of amino acid residues in the relevant portions of the molecule, or structural homology. Pepsin shares structural homology with HIV and other aspartic proteases. Campos and Sancho, "The active site of pepsin is formed in the intermediate conformation dominant at mildly acidic pH," FEBS Letters Vol. 538:89-95 (2003).

The invention provides several uses for the peptides. Examples of possible uses include a diagnostic assay and a therapeutic agent. IPF causes a dramatic rise in cytokines (e.g. interleukin 9 and 10) and antibodies to p24 antigen in HIV patients.

The properties of the peptides identified as part of the IPF herein include MW, inactivity at neutral pH, as present in blood, and their partial sequence data. Also, the IPF fragments migrate as a single main peak in HPLC, such as shown in the chromatogram of FIG. 1 for IPF-6, with a particular retention time. Because pepsin is inactivated during isolation of IPF, the preparation is stable and does not degrade significantly over time.

The inactivated pepsin fragments (IPF) of the invention may be referred to as irreversibly-inactivated. This is due to its treatment at neutral pH. As noted above, inactivation occurs above about pH 5, and becomes irreversible above about pH 6, and proteolytic activity is lost by such treatment. Maximal activity of pepsin as an enzyme is between 2-4 pH. The inventive method increases the pH of diluted pepsin to above 5, above about 6, and desirably in the range of pH 6.6-6.8 before precipitation and during use. Thus IPF formulation pepsin fragments are irreversibly inactivated.

The treatment, fragmentation, and isolation procedures inactivate pepsin and cut the pepsin chain into separate peptide fragments. IPF may be isolated from active pepsin. For example, Sigma porcine pepsin P7000 may be used. This is a pepsin A from porcine gastric mucosa, is a powder with 800-2,500 units/mg protein. The CAS number is 9001-75-6, and the EC number is 3.4.23.1. According to Sigma, it preferentially cleaves C-terminal to Phe, Leu and Glu. It does not cleave at Val, Ala or Gly. Optimum pH is 2-4. Stable at 60° C. Pepsin is irreversibly inactived at pH >6 and has a mol wt 35 kDa. See, Harlow, E., and Lane, D., *Antibodies: A Laboratory Manual*, Cold Spring Harbor, N.Y. (1988), 626-628; and *Merck* 13, 7225.

The IPF 45 kD peptide and IPF 15 kD peptide have amino acid sequences homologous to pepsin, meaning that at least about 5, 10, 15, or 20 of the amino acid residues in the peptide are identical to those of pepsin.

As used herein, the present invention may be directed to modulating immune system activity, which includes treating, decreasing, increasing, attenuating or modulating any condition that may benefit from an enhancement of immune system activity. Immune conditions can include immune diseases or disorders. Immune disorders may include Allergies, Auto-Immune, DiGeorge Syndrome, Familial Mediterranean Fever, Immune Deficiency, and Multiple Chemical Sensitivity.

Immune system disease or disorder may include at least one of Agammaglobulinemia, Anaphylaxis, Antiphospholipid Syndrome, Ataxia Telangiectasia, Autoimmune Diseases, Common Variable Immunodeficiency, DiGeorge Syndrome, Electrosensitivity, Familial Mediterranean Fever, Graft vs Host Disease, Granulomatous Disease, Chronic, HIV Infections, Hypersensitivity, Hypersensitivity, Immediate, IgA Deficiency, Immune Complex Diseases, Immune System Diseases, Immunologic Deficiency Syndromes, Lambert-Eaton Myasthenic Syndrome, Lambert-Eaton Myasthenic Syndrome, Latex Hypersensitivity, Lymphoproliferative Disorders, Multiple Chemical Sensitivity, Purpura, Schoenlein-Henoch, Samter's Syndrome, Severe Combined Immunodeficiency, Sick Building Syndrome, Sjogren's Syndrome, and Wiskott-Aldrich Syndrome.

In one aspect of the invention, auto-immune disorder may comprise Addison's, Ankylosing Spondylitis, Antiphospholipid Syndrome, Barth Syndrome, Graves' Disease, Hemolytic Anemia, IgA Nephropathy, Lupus Erythematosus, Systemic, Microscopic Polyangiitis, Multiple Sclerosis, Myasthenia Gravis, Myositis, Osteoporosis, Pemphigus, Psoriasis, Rheumatoid Arthritis, Sarcoidosis, Scleroderma and Sjogren's Syndrome. Examples of allergies may include Asthma, Food, Hay Fever—Rhinitis, Hives, Latex and Sinusitis. In yet another embodiment, the patient may have AIDS or AIDS Related Complex, multiple sclerosis, hepatitis, herpes, rheumatoid arthritis, autoimmune diabetes, encephalomyelitis or another autoimmune disease.

In another exemplary embodiment, the present invention may encompass a cancer preventive or therapeutic vaccine.

In yet another exemplary embodiment, the IPF is administered with at least one other polynucleotide, like a molecular adjuvant, for cancer preventive or therapeutic vaccine. The cancer can be either primary or metastatic and may include renal cell carcinoma (kidney cancer), melanoma, pancreatic cancer, non-Hodgkin's lymphoma, lung carcinoma, prostate cancer, spinal cell carcinoma, soft tissue sarcoma or fibrosarcoma.

Compositions comprising the IPF fractions disclosed herein may also be used to treat hepatitis, multiple sclerosis, lupus, and herpes simplex. Anecdotal observations, backed up by blood work, indicate a reduction in severity of symptoms in patients with these diseases, and predicts efficacy in other viral and autoimmune diseases.

In an exemplary embodiment, IPF peptides, e.g. IPF1-6, show specific binding and indicate usefulness as a) a diagnostic and b) a therapeutic for HIV, and other diseases. The binding of this protein material with envelope proteins in several infectious diseases as well as direct binding to CD4 cells indicates that IPF can stimulate an immunological reaction, for example by promoting the formation of superantigens which increase production of specific antibodies.

Diagnostic methods using IPF may be performed by combining IPF with test and control sera and conducting 2-D electrophoresis in 1% agarose gels, following the techniques set forth in Zhabilov et al. (US 2004/0018639, filed 3 Jun. 2003 by Zhabilov, Harry P. et al. and incorporated herein by reference), with modifications apparent to a person of ordinary skill. Therapeutic methods using IPF disclosed herein are performed by administering IPF pharmaceutical compositions to a subject having a disease susceptible to treatment with IPF. The formulations, dosages, dosing regimen, and routes of administering may be those described in Zhabilov et al. or other examples apparent to a person of ordinary skill.

In another exemplary embodiment, the IPF composition may be in a variety of forms, e.g., a pharmaceutical composition. In one aspect, the pharmaceutical composition may comprise the IPF disclosed herein and a pharmaceutically effective carrier, e.g., buffered saline, water, aluminum hydroxide, or another suitable adjuvant.

In yet another exemplary embodiment, the composition may contain preservatives, vehicles, buffers, tonicity adjusters, chelating agents, antioxidants and or other material. Examples of preservatives include Phenylethyl alcohol USP, Sorbic Acid NF, Sodium Propionate, Sodium Benzoate NF, and Benzyl alcohol NF. Examples of Vehicles include Purified Water USP, Hydroxy Ethyl Cellulose NF, Polyethylene Glycol NF, Povidone USP, Hydroxypropyl Methylcellulose F4M USP, Dextran 70 USP, Poloxamer NF, Polyoxyl-40-Stearate USP and Aluminum Chloride. Examples of buffers include Sodium Phosphate (mono, di and tribasic), Sodium Carbonate, Sodium Biphosphate, Sodium Bicarbonate USP, Citric Acid Monohydrate USP, Acetic Acid, Sodium Citrate USP, Phosphoric Acid, Glacial Acetic Acid USP, Sodium Hydroxide NF, Sodium Acetate USP, Potassium Citrate USP, Hydrochloric Acid NF, and Potassium Phosphates: (mono, di and tribasic). Examples of tonicity adjusters include Sodium Chloride USP, Dextrose USP, Glycerin USP, Potassium Chloride USP and Mannitol USP. Examples of chelating agents include Edetate Disodium USP, Edetate Monosodium, Edetic Acid NF, and Edetate Trisodium. Examples of antioxidants include Sodium Metabisulfite NF, Sodium Bisulfite, Sodium Thiosulfate USP, and Acetylcysteine USP. Other material may include Polysorbates (20-85) NF, Pluronic F168, Pluronic F127, and Polyethylene Glycol 300, 400, 6000 NF.

The IPF compositions disclosed herein may be administered in a variety of manners, e.g., orally, by inhalation, intradermally, intramuscularly, subcutaneously or intravenously. It may be in the form of an injectable solution or formulation, tablet, liquid formulation, lyophilized or aerosolized receptors.

In one embodiment, the IPF compositions disclosed herein are administered intramuscularly. Also, doses may be administered at least daily, weekly or monthly, for as long as treatment is required. In exemplary embodiments, the IPF is administered intramuscularly once a week for six week, twice weekly for eight weeks, or as sixteen injections with two injections on consecutive days per week for eight weeks.

The IPF disclosed herein may be administered via the composition in a variety of doses, e.g., from about 1 to about 25 mg of per 1 ml of the composition. In an exemplary embodiment, the IPF is administered in about 8 mg or about 4 mg per 2 ml of formulation. The IPF may be administered in an amount of 57 μg per 1 kg of body weight of the patient. In mice, e.g., IPF can be administered from about 0.1 to about 0.5 mg/kg of body weight and in rabbits, about 1.24 mg/kg, twice weekly for eight weeks.

The IPF disclosed herein may have one or more of the following effects: suppressing tumor immunity or eliciting protective immunity against tumor cells, chaperoning immune enhancing agents and peptides, activating dendrites and macrophages by modulating inflammatory cytokines and inducing maturation of dendrites, modulating release of IL-12 and tumor necrosis factor $\alpha$ (TNF$\alpha$), inducing anti-tumor activity and tumor-specific cytolytic T-cells and inducing cancer-specific $CD8^+$ T-cell response.

The IPF components disclosed herein may have one or more of the following phenotypic effects: increasing the CD4+ CD45 RO+ CD62 L population, increasing in CD4+ CD45 RA+ CD62 L population, inducing a second CD4+ population having lower CD4 intensity but no increase in SSC, inducing a parallel increase in absolute CD4 cell counts when this phenomenon appears, and increasing the CD8+ CCR5+ population.

The IPF component may have one or more of the following functional effects over time: increasing the IFN-γ containing CD3+ CD4+ cells post stimulation in vitro, decreasing the IL-4 containing CD3+ CD4+ cells post stimulation, and increasing the IFN-γ containing CD3+ CD8+ cells over time.

DETAILED DESCRIPTION OF THE INVENTION

Pepsins (of which there are several isozymes) are the principal proteases in gastric secretions of adult mammals. They belong to the family of aspartic proteases and are synthesized and secreted by cells in the gastric mucosa as inactive enzyme-precursors consisting of a signal peptide, an activation peptide and an occluded active enzyme. En route to the lumen of the stomach for protein digestion, the signal peptide is cleaved to yield the inactive proenzyme pepsinogen, which, on exposure to a low gastric pH (<4), cleaves in turn to yield mature, catalytically active pepsin.

Porcine pepsin was one of the first enzymes to be studied, and is perhaps the best-understood aspartic protease. It has 327 amino acid (aa) residues, and a molecular mass of 34 kDa (PNAS (U.S.) 70:3437-39 1973). Proteolytic activity of pepsin is at its highest at a pH of about 1.8 to 3.5; it is inactivated at a pH of about 5 and irreversibly inactivated (denatured) at a pH of about 6-7. Owing to their importance, amino acid residues associated with the substrate binding (active) site have been a research focal point. However, it is apparently still not clear how much functional activity, if any, is influenced by the remainder of the peptide.

The family of aspartic proteases (aspartases) is characterized by aspartic acid residues at their active (catalytic) sites. Human pepsin, for example, has two active site aspartate residues (coded "D" or "Asp"). This family also includes the HIV protease (and its numerous variants), comprising two identical chains each having a single active-site aspartate residue. Essential for maturation of the newly synthesized virus, which is expressed as a polyprotein, this protease has become a popular target for researchers attempting to block HIV replication.

Certain embodiments of the present invention are generally directed to providing isolated peptides characterized by, respectively, the amino acid sequences TLTSGGGAIALPPSMAAPPLGPVAPLTGAIHAPTXG (SEQ ID NO: 1), a fragment of approximately 45 kDa; TLSTATGGAIPPVAAMPPGLVAPTHGPAIHP (SEQ ID NO: 2); NXVPVSVEGYXQITLDSITX (SEQ ID NO: 3), a fragment of approximately 13.5 kDa; MTLTTGSGAIAPAMPPGLP- PHTGAIHAPM (SEQ ID NO: 4); and CCATSGPC-GAVMILTPHLTA (SEQ ID NO: 5), and a significant in vitro binding affinity for gp96. The peptides, referred to herein as, respectively, IPF-1, IPF-2, IPF-3, IPF-4 and IPF-5 (Inactivated Pepsinogen Fragments-1-5), were isolated from porcine pepsinogen, purified, and irreversibly inactivated for use in cancer therapeutic procedures.

The present invention also encompasses a cancer preventive or therapeutic vaccine comprising IPFgp96, and more specifically IPF-1gp96; IPF-2gp96; IPF-3gp96, IPF-4gp96 and IPF-5gp96 or combinations thereof, which may be mixed with one or more polynucleotides encoding a molecular adjuvant. Any molecular adjuvant that increases cellular immune response may be used like cytokine IL-2. Administration may be via an intramuscular injection. The cancer to be treated may be primary or metastatic and the patients to be treated may have multiple different types of cancer.

The heat shock protein, e.g., gp96, may be prepared according to suitable methods known in the art, such as according to the methods set forth in Chandawarkar, et al. (Int'l Immunology, Vol. 16, No. 4, 615-624 (2004)), incorporated in its entirety by this reference. Complexes comprising HSP and IPF may be prepared according to suitable methods known in the art, such as disclosed in application No. PCT/US2006/038045, also incorporated in its entirety by this reference.

Figure 9:
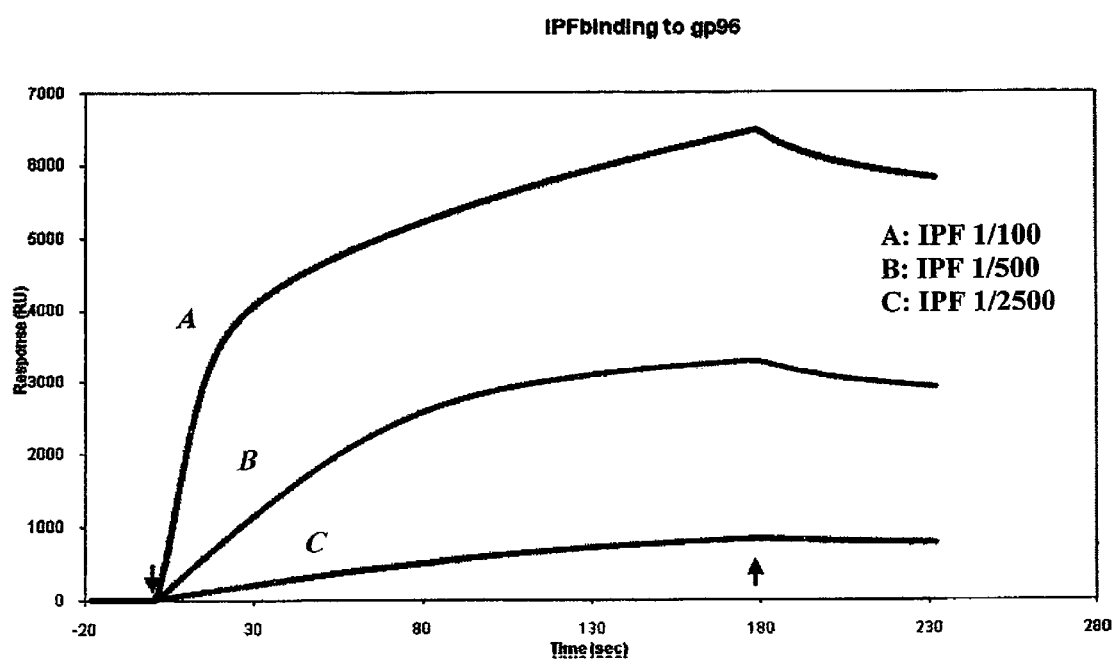
FIG. 9 is a graph showing binding of an IPF with heat shock protein gp96 at dilutions of IPF 1/2500, IPF 1/500 and IPF 1/100, according to one embodiment of the invention.

FIG. 9 is a graph showing binding of an IPF with heat shock protein gp96 at dilutions of IPF 1/2500, IPF 1/500 and IPF 1/100, according to one embodiment of the invention. A number of approaches may be used to detect complexing between IPF and gp96. By way of example, one such approach may be to obtain specific antibodies against IPF and gp96 and to build a sandwich immunoassay by suitable methods known in the art to detect the presence of these protein complexes. To detect binding of gp96 to IPF, the antigen may be coated on a plate to capture proteins from the sample and then report the binding with a specific detection antibody. The secondary (or detection) antibody may be directly labeled with MSD SULFO-TAG NHS ester or a SULFO-TAG-labeled anti-species, e.g., anti-mouse if the detection antibody is raised in mouse and the detection antibody is raised in a different species than the capture or primary antibody. Antibodies specific to IPF-gp96 complexes may also be used.

The cancer preventive vaccine may comprise a clear liquid opalescent suspension of spontaneous precipitate IPF (e.g., IPF-1, IPF-2, IPF-3, IPF-4 and/or IPF-5) and gp96 molecules with IL2 as adjuvant and may comprise complexes of IPF-1, IPF-2, IPF-3, IPF-4 and IPF-5 and gp96. Activity is preferably 1:0.6 measured by the ability of IPF to bind with gp96 (e.g., three molecules of IPF bound two molecules of gp96). The cancer preventive vaccine may be injected intramuscularly one injection per week for six weeks. The immune response probably gives evidence of two actions: 1) cytotoxic effect against tumor cells (cytotoxic T lymphocytes (CTLs) are effectors of CD8+ that can mediate the lysis of target cells bearing antigenic peptides associated with a MHC molecule. Other cytotoxic cells include gamma/delta chain and CD4+ NK 1.1+ cells); and 2) increased antibody production.

Other embodiments of the present invention are generally directed to providing an isolated antiviral peptide characterized by the amino acid sequence GDEPLENYLDTEYF (SEQ ID NO: 6) (-Gly-Asp-Glu-Pro-Leu-Glu-Asn-Tyr-Leu-Asp-Thr-Glu-Tyr-Phe-) ("IPF-6") and a significant in vitro binding affinity for HIV-1 gp120, gp 41 and human CD4 cells. The peptide has anti-retroviral activity in vivo, particularly anti-HIV-1 activity. The peptide, referred to herein as IPF-6 (Inactivated Pepsinogen Fragment-6), was isolated from porcine pepsinogen, purified, and irreversibly inactivated for use in HIV-1 prophylactic, therapeutic and diagnostic procedures. IPF-6 is expected to have anti-retroviral activity in vivo, particularly inhibition of HIV-1 entry into human CD4+ cells.

The exemplified peptide was obtained from porcine pepsinogen (FIG. 1) by isolation from a 45 kDa band of IPF preparation under gel electrophoresis (FIG. 2). It may also be derived from pepsinogen from any other source containing this sequence, or from any other peptides or proteins containing this sequence whereby suitable source pepsinogens are readily available commercially. Common laboratory methods and reagents for selectively cleaving intact proteins and for isolating and sequencing the cleaved peptides, such as the Erdman degradation process, may be used. The peptide may also be produced by peptide synthesis, using conventional methods. Moreover, genetically engineered constructs expressing the sequence of interest are generally preferred, although chemical syntheses may also be used.

Figure 3:
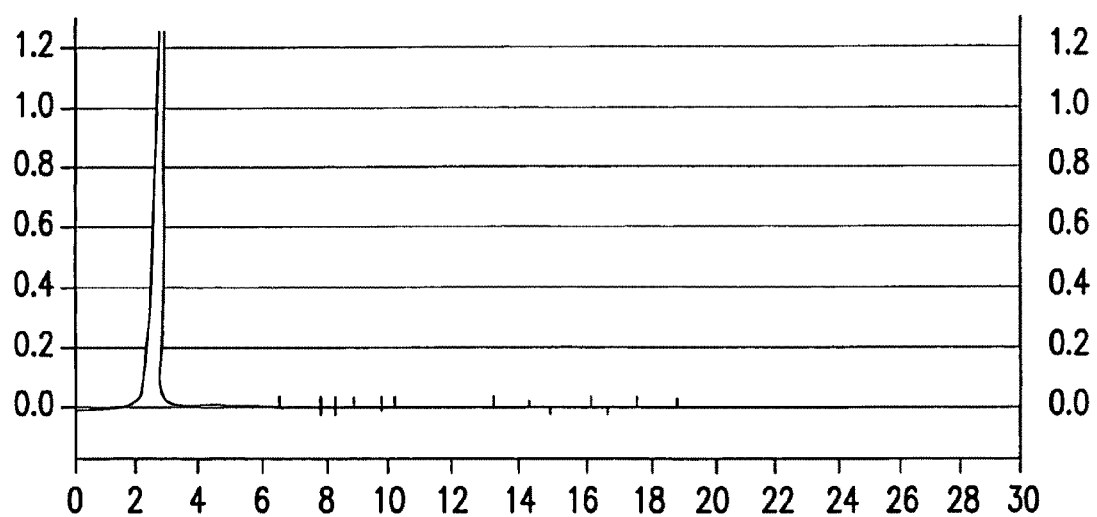
FIG. 3 is a Biacore graph showing a HPLC (High Performance Liquid Chromatography) chromatogram of an isolated IPF in accordance with once aspect of the present invention.
Figure 4:
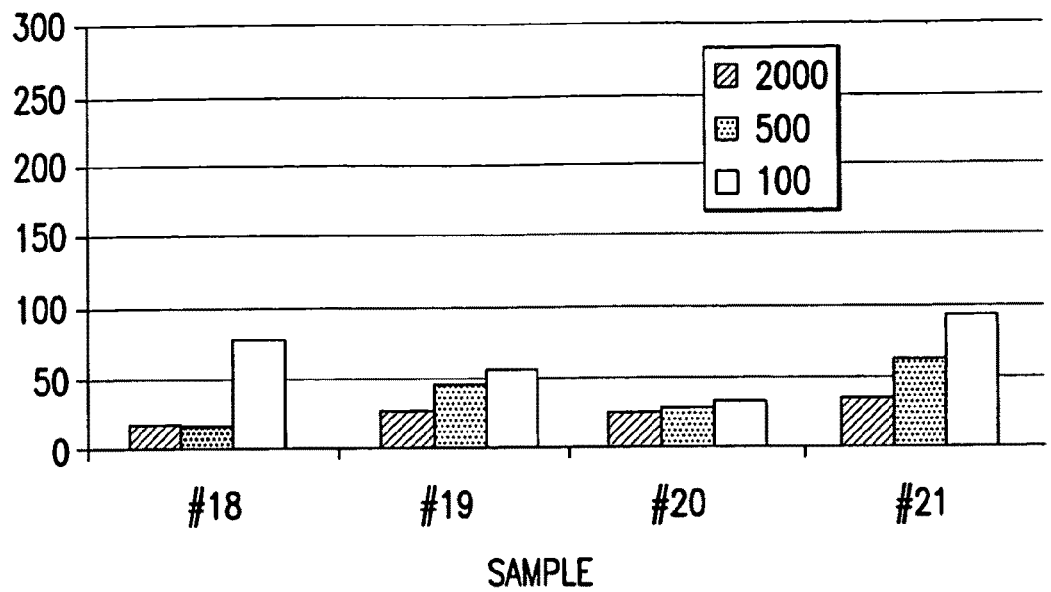
FIGS. 4, 5, 6, and 7 illustrate exemplary binding of four samples of IPF with gp41, gp120, human CD4, and human serum at 3 different dilutions.
Figure 5:
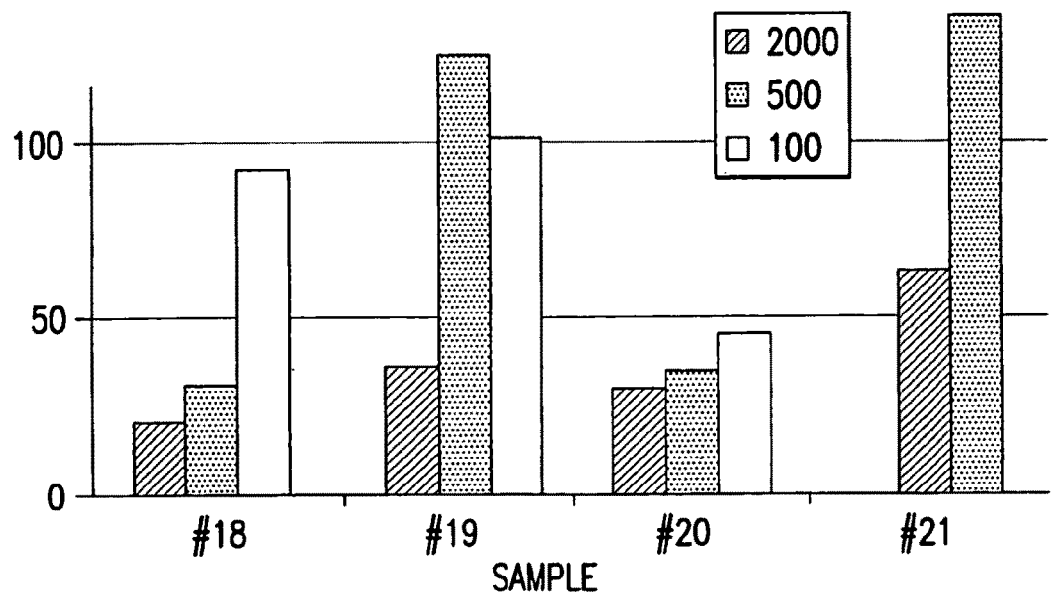

The peptides in the IPF fractions may be isolated and concentrated by any one of several techniques well-known to those skilled in the art, such as ammonium sulfate precipitation. The produced peptide isolate may be purified by standard processes such as gel filtration and RP-HPLC, and inactivated by exposure to a neutral-to-alkaline environment of about pH 6.5 or greater or as otherwise known in the art. The peptide may also be alkylated to increase immunogenicity if desired, for example, by the process described for methylation in U.S. Patent Application Publication US 2004/0018639 A1. A HPLC chromatogram of the purified, inactivated IPF-6 product in one embodiment of the invention is shown in FIG. 3.

Homologues or analogues of the sequence which conserve at least critical binding site amino acid structures and functions and also conserve any distal structural/functional residues essential for binding activity as described herein may be substituted for the IPF of SEQ ID NOS: 1-6 (IPF-1-IPF-6. Variants of the sequences, including chemically modified derivatives, having a high sequence similarity will be generally preferred, provided that binding activity is not significantly adversely affected. Residues superfluous to the disclosed function of the peptides of the invention may be deleted or added with the same proviso. Modified sequences may be evaluated for conserved binding activity by, for example, following the binding assays described herein or in the literature. Numerous databanks are accessible for protein sequence analysis, such as those which combine sequence similarity with fold recognition to predict functional equivalents. Binding properties (affinity, specificity, etc.) may also be evaluated by the binding assays described below or other conventional assays, as known in the art.

Figure 6:
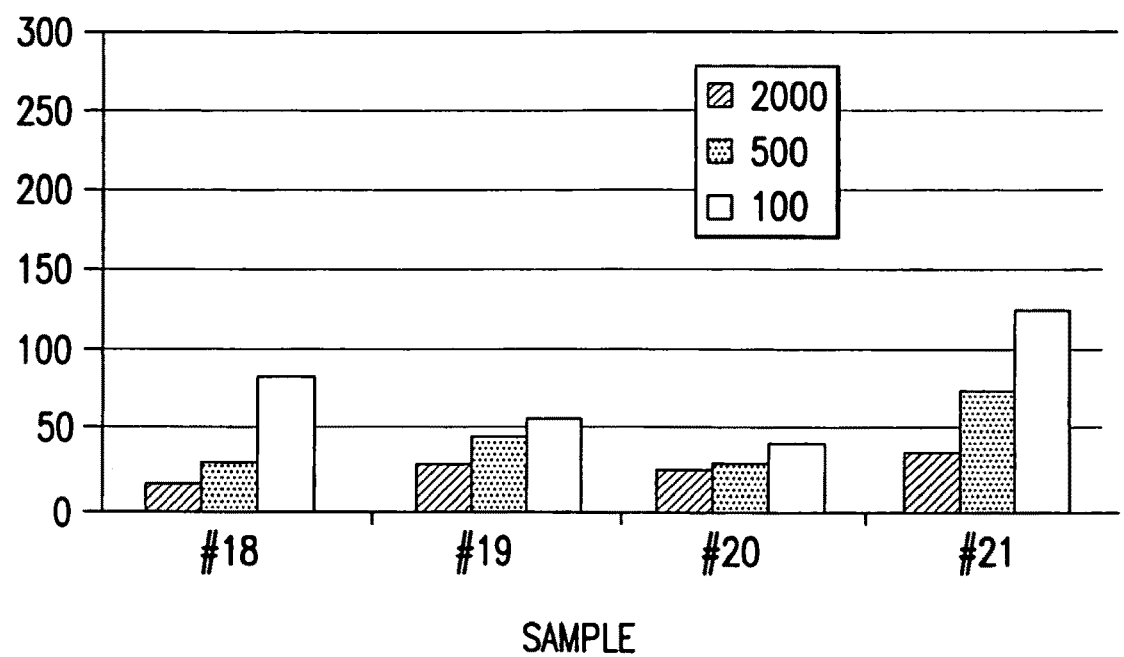
Figure 7:
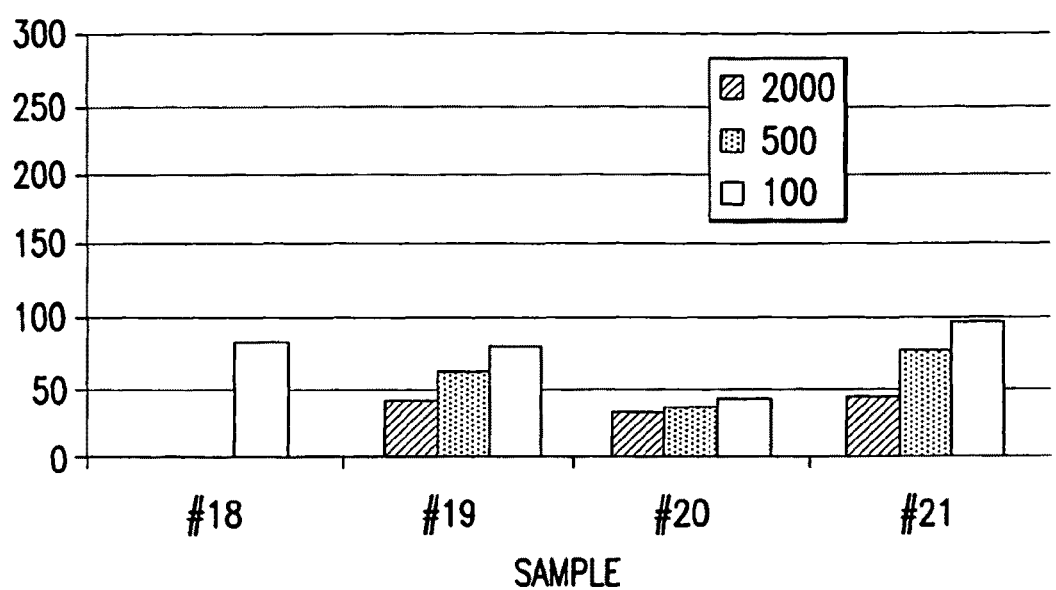
Figure 8:
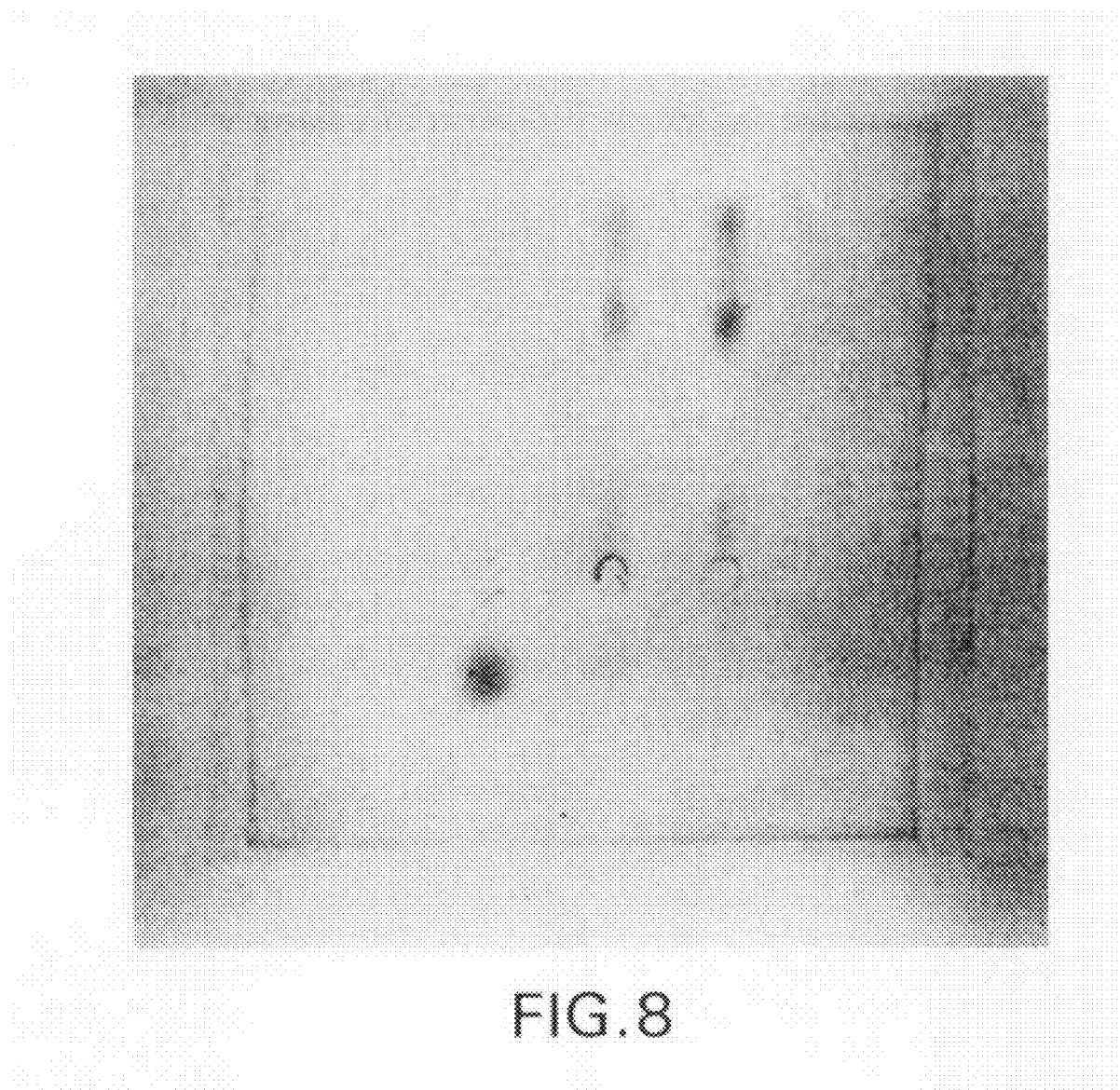
FIG. 8 is a photograph of an electrophoresis agarose gel showing bound IPF and gp41.

BIACORE assays were used for binding affinity. See FIG. 6. This technology measures mass concentration of biomolecules close to a surface. The surface is made specific by attaching one of the interacting partners. Sample containing the other partner(s) flows over the surface: when molecules from the sample bind to the interactant attached to the surface, the local concentration changes and an SPR (surface plasmon resonance) response is measured. The response is directly proportional to the mass of molecules that bind to the surface. The SPR response can be expressed by resonance units (RU). One RU represents change of 0.0001 in the angle of the intensity minimum which is equivalent to a change in concentration of 1 pg/mm.

The exact conversion factor between RU and surface concentration depends on properties of the sensor surface and the nature of the molecule responsible for the concentration change. Assays tracking the binding of IPF with CD4 cells, gp41, gp120, and human sera are very important to detect the formation of the super antigen responsible for the specific immune response. That is, the high response of IPF fragments, measured in Response Units, indicates a high utility as a specific binding agent for components of HIV.

IPF-6 demonstrates binding in vitro with nonglycolysed fragment 579-601 of the HIV-1 envelope protein gp41 subunit, with gp120 HIV-1 subunit, with human CD4+ cells and with human serum under gel electrophoresis (Biocor method) (see, FIGS. 4-8). The assays for these bindings were conducted by The Institute for Molecular Medicine using standard protocols. The spontaneous binding of IPF-6 with the gp41 subunit is a particularly important biological property. Separately, under simple agarose electrophoresis, IPF-6 and gp41 move in opposite directions. However, when they are mixed prior to electrophoresis, gp41 changes direction and takes the direction of IPF-6. Quantitative analysis showed that the binding capacity ratio of IPF-6 to gp41 was 1:0.66. That is, three molecules of IPF-6 bound two molecules of gp41 to form a complex which may function in vivo as, for example, a superantigen with significant anti-HIV-1 biological activity. Such antigen can be used as a bioassay reagent, in the production of mono- or polyclonal antibodies, in the manufacture of vaccines, and in other applications wherein antigens are conventionally employed.

While the mechanism of these binding events is not completely understood, it is contemplated that exposure of HIV-1 to the IPF-6 of the present invention will effectively block gp41 and gp120 domains essential for viral entry into CD4+ cells and inhibit viral infection, in vivo and in vitro. It is also contemplated that the IPF-6 of the present invention will effectively compete with HIV-1 for its CD4+ cell surface binding sites and inhibit virus entry into these cells, in vivo and in vitro. Various in vitro protocols are known in the art for predicting in vivo antiviral activity of compounds for inhibiting replication of HIV, and these protocols may be used in connection with the practice of the present invention. Exemplary art-recognized anti-HIV screening assays are cited in U.S. Pat. No. 5,869,522, issued 9 Feb. 1999 to Boyd et al., including those described in *J. Virol. Methods,* 33:87-100, 1991; *J. Natl. Cancer Inst.,* 81:577-586, 1992; *J. Med. Chem.* 35:1978-1986, 1992, and Boyd, M. R., in *AIDS Etiology: Diagnosis, Treatment, and Prevention*, pp305-319 (Lippincott, 1988, DeVita, V. T., Jr., et al., eds).

In accordance with one aspect of the present invention, IPF-6 is used to diagnose viral infection, particularly HIV-1 infection. Bioassays suitable for this purpose are well-known and routine. Typical of these are assays based on competitive binding between, for example, a known amount of a viral protein and a biological sample to be tested for the same viral protein, using an excess of antiviral reagent capable of specifically binding with the known protein, such as an antibody. A mixture of these is incubated and the amount of bound complex calculated and compared to that in a control mixture lacking the sample. The presence, if any, and amount of the viral protein in the sample can then be determined. There are numerous variations on this process, such as sandwich assays, assays with immobilized reagent, assays using labeled reagent (e.g., ELISA, RIA, FIA), and so on. Whatever the variation, whether for detecting or quantifying complex, or for additional reagents, or other modification, they all require a binding agent for the unknown sample. Any of these routine binding assays for quantifying or identifying an unknown sample may thus be used in the practice of the present invention by substituting IPF-6 as the antiviral binding agent for samples to be tested for HIV-1 gp120, gp41, or infected CD4+T-cells.

In accordance with another aspect of the present invention, IPF-6 is used as a prophylactic or therapeutic to prevent or to treat HIV infections. (Herein the term "HIV infections" refers to AIDS and ARC in addition to viral infection per se unless otherwise noted). For in vivo use, the IPF compositions disclosed herein may be prepared for administration by mixing it at the desired degree of purity with a pharmaceutically-acceptable carrier suitable for the route of administration, as well-known in the art. Although the IPF compositions disclosed herein are desirably administered with an adjuvant in some applications, in situations where a series of IPF doses are administered, boosters with the respective IPF may not require adjuvant. Intramuscular or subcutaneous injections are presently the contemplated route for both therapeutic and prophylactic administration of the IPF compositions disclosed herein. However, intravenous delivery, delivery via catheter or other surgical tubing, or other parenteral route may also be used. Alternative routes include oral routes for administering tablets, liquid formulations and the like, as well as inhalation routes. Liquid formulations reconstituted from powder formulations may be utilized. The IPF compositions disclosed herein may also be administered via microspheres, liposomes, or other microparticulates, and via delivery systems or sustained release formulations dispersed in certain tissues including blood.

The dosage administered of the IPF compositions as disclosed herein will depend upon the properties of the formulation employed, e.g., its binding activity and in vivo plasma half-life, the concentration of IPF in the formulation, the administration route, the site and rate of dosage, the clinical tolerance of the patient involved, the patient's condition, and other considerations, as known in the art. Different dosages may be utilized during a series of sequential treatments. The practitioner may administer an initial dose and then boost with relatively smaller doses of IPF. The dosages of the IPF compositions disclosed herein may be combined with other HIV antivirals such as AZT.

EXAMPLES

Isolation and Purification of Irreversibly-Inactive Pepsin Fraction

The following Examples are examples of methods for isolating, purifying, and characterizing the IPF compositions disclosed herein from active pig pepsinogen.

Example I

Isolation and Inactivation of Pepsinogen Fragment

All the buffers and solutions used in this section were sterilized by filtration. If needed, the buffers (0.2 N or 0.1 N HCl) were used to adjust the solutions. All the chemicals, including the distilled water, for the preparation of the buffers and solutions were USP Grade. The ratio of the pepsin to the buffers was 1:4 (weight/weight).

IPF was isolated from active pepsin (Sigma 1:10000) by ammonium sulfate precipitation with centrifugation at about 4° C. The lyophilized pepsin powder was dissolved in 0.14M sodium chloride (NaCl), 0.05M sodium acetate ($CH_3COONa$. $3H_20$), 0.05M sodium citrate ($C_6H_5O_7Na_2.2H_2O$), and 0.20N HCl (pH 2.8-3.2) buffer. The pH of the active pepsin suspension was then increased to 6.2-6.6 and the suspension was incubated for 30 minutes. The suspension was then precipitated with a saturated solution of $(NH_4)_2SO_4$. After degradation, the mixture was centrifuged (8000 RPM at 4° C.) for 60 minutes and the supernatant discarded. The pellet was dissolved in a minimum quantity of 0.14M NaCl, and the resulting solution was dialyzed for 18 hr against dialysis buffer: 0.1M NaCl, 0.1M sodium acetate, and 0.02M thimerozal USP, pH 6.8.

Example II

Purification and Recovery of Irreversibly Inactivated Pepsinogen Fragment

The purification of IPF included the following steps: dialysis, centrifugation, gel filtration, and reversed-phase HPLC.

After dialysis, the low molecular weight dialysate was centrifuged at 15,000 rpm at 4□C for 60 minutes (Beckman rotor) with precipitation of the residual ammonium sulfate. The product was purified by gel filtration to recover purified IPF from the crude mixture, and then purified by filtration on Bio-gel P10 or Sephadex G-75 gels (from Pharmacia Uppsala, Sweden), or 0.2μ SFCA membrane (Nalgene Labware, Rochester, N.Y.). Further purification was achieved by reversed phase high-performance liquid chromatography in an RP-HPLC system GOLD (Beckman) on C-18 columns (RP Ultrasphere 10 mm Spherical 80A Preparative 21.2×150 mm) using gradient 30% acetonitrile diluted in sterile water, HPLC-grade at 15% methanol HPLC-grade mobile phase. Detection 254 nm; flow rate 0.850 ml/min., solvent at pH 6.8. The final purification step included sterile filtration with Nalgen filters 0.45 μ. The HPLC elution profile of the product showed one isolated peak, IPF (see FIG. 3).

Example III

Determination of Molecular Weight

Molecular weight was determined by silver stained 13% non-reducing SDS-PAGE using the Laemmli method (Nature 227-680, 1970). The molecular weight standard demonstrated one peptide with a molecular weight of 45.000 KD (FIG. 2). This band was isolated, and HPLC chromatogram (FIG. 3) confirmed a single peptide in the band.

Example IV

Assessment of Binding Activity

Samples of IPF (#18, 19, 20, and 21) were used to detect binding with gp120, gp41, CD4+ cells, and serum from a healthy patient. New chips were coated with these proteins and Biacore assays for binding activity were performed. These samples were diluted to 1:2000, 1:500 and 1:100. The results are shown in FIGS. 4, 5, 6, and 7. Sample #21 bound to all target proteins better than the other samples. The assay used a Biacore (Biacore AB, Uppsala, Sweden) system based on sensor chips which provide surface conditions for attaching molecules of interest, a microfluidic flow system for delivering samples to the surface, and a surface plasma response (SPR) which detects mass concentration at the surface. SPR-based biosensors monitor interactions by measuring the mass of molecules bound to the surface. This response is expressed by resonance units (RU), whereby a change in concentration of 1 pg/mm is equivalent to a change of 0.0001 in the angle of intensity minimum, which equals one RU. The exact conversion factor between RU depends upon the properties of the sensor surface and the nature of the molecule responsible for the change in concentration. The assays demonstrate the formation of superantigen for provoking immune response.

Example V

UV Absorption

Circular dichroism (CD) provides information about the secondary structure of optically active materials. The far-UV or amide region (170-250 nm) is dominated by contributions of the peptide bonds, whereas CD bands in the near-UV region (250-300 nm) originate from the aromatic amino acids. The UV region of IPF was in the range of 252-260 nm.

Example VI

Methylation of IPF

The purified IPF was methylated to form a methylated IPF preparation as follows. IPF was mixed with CH2BrCOOH in sufficient quantity to produce a final solution of 0.2 M CH2BrCOOH. For example, 2.78 g CH2BrCOOH was dissolved in 10 ml distilled water and added to 100 ml IPF from the HPLC purification step, containing 700 mg IPF (7 mg/ml). The pH of the mixture was adjusted to and maintained at 7.2 with 0.1 M NaOH. The mixture was allowed to incubate from 6 to 8 hours. The IPF protein in the resulting aqueous fragment was concentrated by ammonium sulfate precipitation, using techniques known in the art. To 10 ml of the methylated IPF was added an equal volume of saturated ammonium sulfate. The mixture was refrigerated at 4 C for 12 hours and then centrifuged at 15000 rpm for 60 minutes. The pellet was removed and dissolved in final buffer containing 0.1M NaCl, 0.1M sodium citrate, and 0.02M thiodiglycol. The mixture was then dialyzed against the same buffer, to remove ammonium sulfate, for 24 hours.

Methylated IPF is lyophilized to form a slightly yellow powder. It is stable at room temperature but is preferably stored under refrigeration. The molecular weight of the IPF fragment was determined by silver stained 13% non-reducing SDS-PAGE (sodium dodecyl sulfate-polyacrylamide gel electrophoresis) using the Laemmli method (Laemmli, U. K., Nature, 227:680 (1970)). Standards were: bovine serum albumin (66,000 molecular weight, MW); porcine heart fumarose (48,500 MW); bovine erythrocytes carbonic anhydrase (29,000 MW); bovine milk beta-lactoglobulin (18,400 MW); and bovine milk α-lactalbumin (14,200 MW). The isoelectric point of the IPF composition is about 6.2 as determined by isoelectric focusing. Pepsin, in contrast, has a low pI.

Example VII

Adjuvant

The IPF may be formulated in an aluminum hydroxide adjuvant. 1 ml of an IPF formulation contains: 4 mg IPF, 0.016 M AlP0.sub.4 (or 0.5 mg Al.sup.3+), 0.14 M NaCl, 0.004 M CH.sub.3COONa, 0.004 M KCl, pH 6.2. ALUM-aluminum hydroxide; Al(OH)3. Aluminum hydroxide is a widely used adjuvant, especially in commercial products such as vaccines. It is very well suited for strong antigens. Many sources of aluminum hydroxides are available, e.g. Alhydrogel, Accurate Chemical & Scientific Co., Westbury, N.Y.

Example VIII

Preparation of IPF Injection for Treating HIV

The inactivated pepsin fragment suspension may be prepared for injecting a preparation of highly purified inactivated pepsin fragment, such as the IPF-6 fragment with a molecular weight of 45 KDa.

For example, the formulation may comprise (w/v) 0.4% inactivated pepsin fragment, 0.23% aluminum phosphate U.S.P., 1.29% sodium citrate U.S.P., 0.41% sodium acetate U.S.P. and water for injection to 100%. For a 1000 ml batch: place 900 ml of U.S.P. sterile water into container, preferably glass. Add 12.9 g sodium citrate and mix until dissolved. Add 4.1 sodium acetate and mix until dissolved. Add 4 g inactivated pepsin fragment, mix until a homogenous clear solution is obtained. Filter the resulting solution through a sterile 02. μm filter into a sterile depyrogenated 2 liter container with a sterile magnetic stirrer. Sterile filter 55 ml of 0.016 M trisodium phosphate solution into the above 2 liter sterile container. Sterile filter 50 ml of 0.016 M aluminum chloride solution into the 2 liter container, with the aluminum chloride being dispensed at a steady, drop by drop rate. Stir the resulting inactivated pepsin fragment suspension for 30 minutes at room temperature. Continue stirring for another 6 hours at 4° C. The sterile inactivated pepsin fragment suspension is ready to be filled into sterile 3 ml borosilicate vials.

The final 1 ml of the final IPF formulation may contain: 4 mg IPF (purity preferably >96%±0.290); 2.26 mg 0.016M $AlPO_4$ (or 0.5 mg $Al^{+3}$); 4.1 mg 0.004M $CH_3COONa$ (sodium acetate); and 12.9 mg $C_6H_5O_7$ (sodium citrate); pH 6.2. In yet a further embodiment, the formulation may comprise per vial, about 8 mg IPF, 4:52 mg aluminum phosphate, 1.0 mg aluminum, 25.8 mg sodium citrate and 8.2 mg sodium acetate. In one regimen, 2 ml of this formulation makes up one vial with the dosage per patient per day being 16 vials. During the regimen, the patient should be monitored to assess the effectiveness of the regimen. CD+4 cell counts are useful and common methodology for evaluating HIV infection, as are assays for antibody or T-cell titers.

Example IX

IPF Formulation and Adminstration

The following is an example of a contemplated IPF formulation, dosage and administration schedule, which may be used with the IPF compositions disclosed herein:

The patient is administered an intramuscular injection containing 8 mg of the IPF composition (preferably 2 ml of a formulation containing 6 mg/ml of IPF in a pharmaceutically acceptable solution) or 57 μg of IPF protein per kg body weight of the patient. Each treatment course consists of 16 injections, with two injections on consecutive days per week for 8 weeks. Three months after the last injection, if the patient's condition warrants, the treatment regimen is repeated. The treatment regimen may be repeated until satisfactory results are obtained, e.g., a halt or delay in the progress of the infection or disease, an alleviation of the infection or disease, or a cure is obtained. Preferably, in this application, IPF will be formulated with an aluminum hydroxide adjuvant.

Example X

Table 1 includes data from a preliminary study of a 54 year-old male patient with $4^{th}$ stage pancreatic carcinoma treated with two cycles of treatment with IPF, which were administered to the patient in September, 2008. Unenhanced images of the liver were obtained at 5 mm interval and thickness. Following bolus of IV infusion of 125 ml of nonionic contrast (Isovue 370) parameters used were: abdomen and pelvis 5 mm thick helical scans; axial reconstructions were obtained at 2.5 mm slice thickness and 2 mm slice interval; patient received oral contast. Prior examination was on Apr. 18, 2008. In this study, the full treatment comprises three cycles of 16 vials of IPF each cycle.

In the second examination, tumor measurement was obtained with a CT scan done in November 2008. CT scan of the abdomen with limited imaging through the lower lungs showed that the patient had two very small focal densities in the right middle lobe likle atelectasis. No pleural effusion were seen. In the liver is significant for multiple hypodesnse lesions consistent with metastases. Many of these appear to decrease slightly in size when compared to the prior examination. The lesion in the posterior right lobe currently measures 35×22 mm. Previously it measured 43×33 mm. A lesion in the anterior left lobe currently measures 18×17 mm. previously it measured 26×25. The other lesions all appeared to decrease in size. There was a hypodense lesion seen in the spleen slightly decreased consistent with a metastatic lesion. The pancreatic mass was not well demonstrated due to adjacent stomach. It measured approximately 40×48 mm slightly decreased in size. The patient has had a prior cholecystectomy. Left adrenal masses were demonstrated suggesting metastases not significantly changed. The kidneys showed normal excretion of contrast bilaterally. A large amount of ascites is present new compared with prior examination.

No definite retroperitoneal lymphadenopathy or pelvic lympadenopathy was demonstrated. Two small focal right middle lobe lung densities were likely atelectasis. Multiple hypodense lesions consistent with metastases all were slightly decreased when compared with the prior examination. Splenic lesion had decreased. Left adrenal masses not significantly changed. Large amount of ascites present. Pancreatic mass poorly demonstrated but likely slightly decreased. The finding on the CT scan showed that most of the lesion in the liver, pancreas and spleen had decreased in size. The patient's CA 19-9 at 19, returned to normal.

The IPF composition used in this study comprised IPF-IL2 adjuvant, specifically the study was done using SEQ ID: NOS. 1 and 2. The Roche Modular E170 CA 19-9 electrochemiluminescent immunoassay was used.

TABLE 1

| Date | Cancer Antigen 19-9, U/mL (ref range: 0-37 U/mL) | Alkaline Phosphatase, U/L (ref range: 38-126) |
| --- | --- | --- |
| Jan. 15, 2008 | 31 | 101 |
| Mar. 07, 2008 | 52 | 143 |
| Mar. 27, 2008 | 116 | * |
| Apr. 24, 2008 | 97 | 235 |
| May 07, 2008 | 52 | * |
| Jun. 03, 2008 | 108 | 133 |
| Jul. 15, 2008 | 68 | 141 |
| Aug. 05, 2008 | 55 | 207 |
| Oct. 07, 2008 | 22 | 95 |
| Nov. 12, 2008 | 19 | 103 |

A person skilled in the art would appreciate that exemplary embodiments described hereinabove are merely illustrative of the general principles of the present invention. Other modifications or variations may be employed that are within the scope of the invention. Thus, by way of example, but not of limitation, alternative configurations may be utilized in accordance with the teachings herein. Accordingly, the drawings and description are illustrative and not meant to be a limitation thereof.

Moreover, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Thus, it is intended that the invention cover all embodiments and variations thereof as long as such embodiments and variations come within the scope of the appended claims and their equivalents.

What is claimed is:

1. An isolated irreversibly inactivated anti-cancer pepsin characterized by the amino acid sequence of SEQ ID NO: 1.

2. A composition comprising the isolated irreversibly inactivated anti-cancer pepsin of claim 1, further comprising a carrier.

3. A composition for inferring immunity against malignant human cells, said composition comprising the composition of claim 2 combined with IL2.

4. A therapeutic composition comprising a complex of the isloated irreversibly inactivated anti-cancer pepsin of claim 1 bound to human gp96.

5. A therapeutic composition comprising a complex of the isloated irreversibly inactivated anti-cancer pepsin of claim 1 bound to a receptor disposed on human gp96.

6. The composition of claim 5, where in the receptor is CD91.

7. A pepsin isolated from a 45 kD pepsinogen fragment, said pepsin consisting of the isolated irreversibly inactivated anti-cancer pepsin of claim 1, wherein said pepsin has a binding affinity for human gp96.

8. A composition comprising the therapeutic composition of claim 4, said composition further comprising IL2.

* * * * *

```
                          SEQUENCE LISTING

<160> NUMBER OF SEQ ID NOS: 31

<210> SEQ ID NO 1
<211> LENGTH: 36
<212> TYPE: PRT
<213> ORGANISM: Sus scrofa
<220> FEATURE:
<221> NAME/KEY: misc_feature
<222> LOCATION: (35)..(35)
<223> OTHER INFORMATION: Xaa can be any naturally occurring amino acid

<400> SEQUENCE: 1

Thr Leu Thr Ser Gly Gly Gly Ala Ile Ala Leu Pro Pro Ser Met Ala
1               5                   10                  15

Ala Pro Pro Leu Gly Pro Val Ala Pro Leu Thr Gly Ala Ile His Ala
            20                  25                  30

Pro Thr Xaa Gly
        35

<210> SEQ ID NO 2
<211> LENGTH: 31
<212> TYPE: PRT
<213> ORGANISM: Sus scrofa

<400> SEQUENCE: 2

Thr Leu Ser Thr Ala Thr Gly Gly Ala Ile Pro Pro Val Ala Ala Met
1               5                   10                  15

Pro Pro Gly Leu Val Ala Pro Thr His Gly Pro Ala Ile His Pro
            20                  25                  30

<210> SEQ ID NO 3
<211> LENGTH: 20
<212> TYPE: PRT
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 3

Asn Xaa Val Pro Val Ser Val Glu Gly Tyr Xaa Gln Ile Thr Leu Asp
1               5                   10                  15

Ser Ile Thr Xaa
            20

<210> SEQ ID NO 4
<211> LENGTH: 29
<212> TYPE: PRT
```

<213> ORGANISM: Sus scrofa

<400> SEQUENCE: 4

Met Thr Leu Thr Thr Gly Ser Gly Ala Ile Ala Pro Ala Met Pro Pro
1               5                   10                  15

Gly Leu Pro Pro His Thr Gly Ala Ile His Ala Pro Met
            20                  25

<210> SEQ ID NO 5
<211> LENGTH: 20
<212> TYPE: PRT
<213> ORGANISM: Sus scrofa

<400> SEQUENCE: 5

Cys Cys Ala Thr Ser Gly Pro Cys Gly Ala Val Met Ile Leu Thr Pro
1               5                   10                  15

His Leu Thr Ala
            20

<210> SEQ ID NO 6
<211> LENGTH: 14
<212> TYPE: PRT
<213> ORGANISM: Sus scrofa

<400> SEQUENCE: 6

Gly Asp Glu Pro Leu Glu Asn Tyr Leu Asp Thr Glu Tyr Phe
1               5                   10

<210> SEQ ID NO 7
<211> LENGTH: 386
<212> TYPE: PRT
<213> ORGANISM: Sus scrofa

<400> SEQUENCE: 7

Met Lys Trp Leu Leu Leu Ser Leu Val Val Leu Ser Glu Cys Leu
1               5                   10                  15

Val Lys Val Pro Leu Val Arg Lys Lys Ser Leu Arg Gln Asn Leu Ile
            20                  25                  30

Lys Asn Gly Lys Leu Lys Asp Phe Leu Lys Thr His Lys His Asn Pro
        35                  40                  45

Ala Ser Lys Tyr Phe Pro Glu Ala Ala Ala Leu Ile Gly Asp Glu Pro
    50                  55                  60

Leu Glu Asn Tyr Leu Asp Thr Glu Tyr Phe Gly Thr Ile Gly Ile Gly
65                  70                  75                  80

Thr Pro Ala Gln Asp Phe Thr Val Ile Phe Asp Thr Gly Ser Ser Asn
                85                  90                  95

Leu Trp Val Pro Ser Val Tyr Cys Ser Ser Leu Ala Cys Ser Asp His
            100                 105                 110

Asn Gln Phe Asn Pro Asp Asp Ser Ser Thr Phe Glu Ala Thr Ser Gln
        115                 120                 125

Glu Leu Ser Ile Thr Tyr Gly Thr Gly Ser Met Thr Gly Ile Leu Gly
    130                 135                 140

Tyr Asp Thr Val Gln Val Gly Ile Ser Asp Thr Asn Gln Ile Phe
145                 150                 155                 160

Gly Leu Ser Glu Thr Glu Pro Gly Ser Phe Leu Tyr Tyr Ala Pro Phe
                165                 170                 175

Asp Gly Ile Leu Gly Leu Ala Tyr Pro Ser Ile Ser Ala Ser Gly Ala
            180                 185                 190

Thr Pro Val Phe Asp Asn Leu Trp Asp Gln Gly Leu Val Ser Gln Asp

```
                195                 200                 205
Leu Phe Ser Val Tyr Leu Ser Ser Asn Asp Asp Ser Gly Ser Val Val
    210                 215                 220

Leu Leu Gly Gly Ile Asp Ser Ser Tyr Tyr Thr Gly Ser Leu Asn Trp
225                 230                 235                 240

Val Pro Val Ser Val Glu Gly Tyr Trp Gln Ile Thr Leu Asp Ser Ile
                245                 250                 255

Thr Met Asp Gly Glu Thr Ile Ala Cys Ser Gly Gly Cys Gln Ala Ile
            260                 265                 270

Val Asp Thr Gly Thr Ser Leu Leu Thr Gly Pro Thr Ser Ala Ile Ala
        275                 280                 285

Ile Asn Ile Gln Ser Asp Ile Gly Ala Ser Glu Asn Ser Asp Gly Glu
    290                 295                 300

Met Val Ile Ser Cys Ser Ser Ile Asp Ser Leu Pro Asp Ile Val Phe
305                 310                 315                 320

Thr Ile Asn Gly Val Gln Tyr Pro Leu Ser Pro Ser Ala Tyr Ile Leu
                325                 330                 335

Gln Asp Asp Asp Ser Cys Thr Ser Gly Phe Glu Gly Met Asp Val Pro
            340                 345                 350

Thr Ser Ser Gly Glu Leu Trp Ile Leu Gly Asp Val Phe Ile Arg Gln
        355                 360                 365

Tyr Tyr Thr Val Phe Asp Arg Ala Asn Asn Lys Val Gly Leu Ala Pro
    370                 375                 380

Val Ala
385

<210> SEQ ID NO 8
<211> LENGTH: 9
<212> TYPE: PRT
<213> ORGANISM: Sus scrofa

<400> SEQUENCE: 8

Thr Leu Tyr Ser Gly Glu Gln Asp Ile
1               5

<210> SEQ ID NO 9
<211> LENGTH: 4
<212> TYPE: PRT
<213> ORGANISM: Sus scrofa

<400> SEQUENCE: 9

Arg Lys Phe Pro
1

<210> SEQ ID NO 10
<211> LENGTH: 5
<212> TYPE: PRT
<213> ORGANISM: Sus scrofa

<400> SEQUENCE: 10

Ser Met Asn Asp Pro
1               5

<210> SEQ ID NO 11
<211> LENGTH: 70
<212> TYPE: PRT
<213> ORGANISM: Sus scrofa

<400> SEQUENCE: 11

Met Lys Trp Leu Leu Leu Leu Ser Leu Val Val Leu Ser Glu Cys Leu
```

```
                1               5                   10                  15
Val Lys Val Pro Leu Val Arg Lys Lys Ser Leu Arg Gln Asn Leu Ile
                        20                  25                  30

Lys Asn Gly Lys Leu Lys Asp Phe Leu Lys Thr His Lys His Asn Pro
                35                  40                  45

Ala Ser Lys Tyr Phe Pro Glu Ala Ala Leu Ile Gly Asp Glu Pro
        50                  55                  60

Leu Glu Asn Tyr Leu Asp
65                  70

<210> SEQ ID NO 12
<211> LENGTH: 11
<212> TYPE: PRT
<213> ORGANISM: Sus scrofa

<400> SEQUENCE: 12

Ile Gly Asp Glu Pro Leu Glu Asn Tyr Leu Asp
1               5                   10

<210> SEQ ID NO 13
<211> LENGTH: 70
<212> TYPE: PRT
<213> ORGANISM: Sus scrofa

<400> SEQUENCE: 13

Thr Glu Tyr Phe Gly Thr Ile Gly Ile Gly Thr Pro Ala Gln Asp Phe
1               5                   10                  15

Thr Val Ile Phe Asp Thr Gly Ser Ser Asn Leu Trp Val Pro Ser Val
                        20                  25                  30

Tyr Cys Ser Ser Leu Ala Cys Ser Asp His Asn Gln Glu Asn Pro Asp
                35                  40                  45

Asp Ser Ser Thr Phe Glu Ala Thr Ser Gln Glu Leu Ser Ile Thr Tyr
        50                  55                  60

Gly Thr Gly Ser Met Thr
65                  70

<210> SEQ ID NO 14
<211> LENGTH: 4
<212> TYPE: PRT
<213> ORGANISM: Sus scrofa

<400> SEQUENCE: 14

Thr Glu Tyr Phe
1

<210> SEQ ID NO 15
<211> LENGTH: 70
<212> TYPE: PRT
<213> ORGANISM: Sus scrofa

<400> SEQUENCE: 15

Gly Ile Leu Gly Tyr Asp Thr Val Gln Val Gly Gly Ile Ser Asp Thr
1               5                   10                  15

Asn Gln Ile Phe Gly Leu Ser Glu Thr Glu Pro Gly Ser Phe Leu Tyr
                        20                  25                  30

Tyr Ala Pro Phe Asp Gly Ile Leu Gly Leu Ala Tyr Pro Ser Ile Ser
                35                  40                  45

Ala Ser Gly Ala Thr Pro Val Phe Asp Asn Leu Trp Asp Gln Gly Leu
        50                  55                  60

Val Ser Gln Asp Leu Phe
```

<210> SEQ ID NO 16
<211> LENGTH: 8
<212> TYPE: PRT
<213> ORGANISM: Sus scrofa

<400> SEQUENCE: 16

Ser Gly Ala Thr Pro Glx Thr Glu
1               5

<210> SEQ ID NO 17
<211> LENGTH: 70
<212> TYPE: PRT
<213> ORGANISM: Sus scrofa

<400> SEQUENCE: 17

Ser Val Tyr Leu Ser Ser Asn Asp Asp Ser Gly Ser Val Val Leu Leu
1               5                   10                  15

Gly Gly Ile Asp Ser Ser Tyr Tyr Thr Gly Ser Leu Asn Trp Val Pro
            20                  25                  30

Val Ser Val Glu Gly Tyr Trp Gln Ile Thr Leu Asp Ser Ile Thr Met
        35                  40                  45

Asp Gly Glu Thr Ile Ala Cys Ser Gly Gly Cys Gln Ala Ile Val Asp
    50                  55                  60

Thr Gly Thr Ser Leu Leu
65                  70

<210> SEQ ID NO 18
<211> LENGTH: 20
<212> TYPE: PRT
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 18

Asn Xaa Val Pro Val Ser Val Glu Gly Tyr Xaa Gln Ile Thr Leu Asp
1               5                   10                  15

Ser Ile Thr Xaa
            20

<210> SEQ ID NO 19
<211> LENGTH: 25
<212> TYPE: PRT
<213> ORGANISM: Sus scrofa

<400> SEQUENCE: 19

Leu Gly Gly Ile Asp Ser Ser Tyr Tyr Thr Gly Ser Leu Asn Trp Val
1               5                   10                  15

Pro Val Ser Val Glu Gly Tyr Trp Gln
            20                  25

<210> SEQ ID NO 20
<211> LENGTH: 28
<212> TYPE: PRT

```
<213> ORGANISM: Sus scrofa

<400> SEQUENCE: 20

Ser Tyr Tyr Thr Gly Ser Leu Asn Ile Arg Val Pro Val Ser Val Glu
1               5                   10                  15

Gly Tyr Trp Gln Ile Thr Leu Asp Ser Ile Thr Met
            20                  25

<210> SEQ ID NO 21
<211> LENGTH: 25
<212> TYPE: PRT
<213> ORGANISM: Sus scrofa

<400> SEQUENCE: 21

Ser Tyr Tyr Thr Gly Ser Leu Asn Trp Val Pro Val Ser Val Glu Gly
1               5                   10                  15

Tyr Trp Gln Ile Thr Leu Asp Ser Ile
            20                  25

<210> SEQ ID NO 22
<211> LENGTH: 25
<212> TYPE: PRT
<213> ORGANISM: Sus scrofa

<400> SEQUENCE: 22

Asn Trp Val Pro Val Ser Val Glu Gly Tyr Trp Gln Ile Thr Leu Asp
1               5                   10                  15

Ser Ile Thr Met Asp Gly Arg Thr Ile
            20                  25

<210> SEQ ID NO 23
<211> LENGTH: 70
<212> TYPE: PRT
<213> ORGANISM: Sus scrofa

<400> SEQUENCE: 23

Thr Gly Pro Thr Ser Ala Ile Ala Ile Asn Ile Gln Ser Asp Ile Gly
1               5                   10                  15

Ala Ser Glu Asn Ser Asp Gly Glu Met Val Ile Ser Cys Ser Ser Ile
            20                  25                  30

Asp Ser Leu Pro Asp Ile Val Phe Thr Ile Asn Gly Val Gln Tyr Pro
        35                  40                  45

Leu Ser Pro Ser Ala Tyr Ile Leu Gln Asp Asp Ser Cys Thr Ser
    50                  55                  60

Gly Phe Glu Gly Asn Met
65              70

<210> SEQ ID NO 24
<211> LENGTH: 36
<212> TYPE: PRT
<213> ORGANISM: Sus scrofa

<400> SEQUENCE: 24

Val Pro Thr Ser Ser Gly Glu Leu Trp Ile Leu Gly Asp Val Phe Ile
1               5                   10                  15

Arg Gln Tyr Tyr Thr Val Phe Asp Arg Ala Asn Asn Lys Val Gly Leu
            20                  25                  30

Ala Pro Val Ala
        35

<210> SEQ ID NO 25
```

-continued

```
<211> LENGTH: 14
<212> TYPE: PRT
<213> ORGANISM: Sus scrofa

<400> SEQUENCE: 25

Gly Asp Glu Pro Leu Glu Asn Tyr Leu Ile Asp Thr Glu Trp
1               5                   10

<210> SEQ ID NO 26
<211> LENGTH: 20
<212> TYPE: PRT
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 26

Asn Xaa Val Pro Val Ser Val Glu Gly Tyr Xaa Gln Ile Thr Leu Asp
1               5                   10                  15

Ser Ile Thr Xaa
            20

<210> SEQ ID NO 27
<211> LENGTH: 7
<212> TYPE: PRT
<213> ORGANISM: Sus scrofa

<400> SEQUENCE: 27

Ser Gly Ala Thr Pro Val Phe
1               5

<210> SEQ ID NO 28
<211> LENGTH: 27
<212> TYPE: PRT
<213> ORGANISM: Sus scrofa

<400> SEQUENCE: 28

Leu Gly Gly Ile Ile Ser Ser Tyr Tyr Thr Gly Ser Leu Asn Trp Val
1               5                   10                  15

Pro Val Ser Val Glu Gly Tyr Trp Gln Ile Thr
            20                  25

<210> SEQ ID NO 29
<211> LENGTH: 27
<212> TYPE: PRT
<213> ORGANISM: Sus scrofa

<400> SEQUENCE: 29

Ser Tyr Tyr Thr Gly Ser Leu Asn Trp Val Pro Val Ser Val Glu Gly
1               5                   10                  15

Tyr Trp Gln Ile Thr Leu Ser Asp Ile Thr Met
            20                  25

<210> SEQ ID NO 30
<211> LENGTH: 25
<212> TYPE: PRT
<213> ORGANISM: Sus scrofa
```

-continued

```
<400> SEQUENCE: 30

Ser Ala Tyr Thr Gly Ser Leu Asn Trp Val Pro Val Ser Val Glu Gly
1               5                   10                  15

Tyr Trp Gln Ile Thr Leu Asp Ser Ile
            20                  25

<210> SEQ ID NO 31
<211> LENGTH: 25
<212> TYPE: PRT
<213> ORGANISM: Sus scrofa

<400> SEQUENCE: 31

Asn Trp Val Pro Val Ser Val Glu Gly Tyr Trp Gln Ile Thr Leu Asp
1               5                   10                  15

Ser Ile Thr Met Asp Gly Arg Thr Ile
            20                  25
```